US009402562B2

(12) United States Patent
Weeden

(10) Patent No.: US 9,402,562 B2
(45) Date of Patent: Aug. 2, 2016

(54) SYSTEMS AND METHODS FOR IMPROVED TRACTOGRAPHIC PROCESSING

(75) Inventor: Van J. Weeden, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 165 days.

(21) Appl. No.: 13/635,575

(22) PCT Filed: Mar. 25, 2011

(86) PCT No.: PCT/US2011/029964
§ 371 (c)(1),
(2), (4) Date: Sep. 17, 2012

(87) PCT Pub. No.: WO2011/119935
PCT Pub. Date: Sep. 29, 2011

(65) Prior Publication Data
US 2013/0004049 A1   Jan. 3, 2013

Related U.S. Application Data

(60) Provisional application No. 61/340,980, filed on Mar. 25, 2010, provisional application No. 61/422,313, filed on Dec. 13, 2010.

(51) Int. Cl.
*G06T 9/00* (2006.01)
*A61B 5/055* (2006.01)
*G06T 7/00* (2006.01)

(52) U.S. Cl.
CPC .............. *A61B 5/055* (2013.01); *G06T 7/0042* (2013.01); *G06T 7/0083* (2013.01); *G06T 2207/10092* (2013.01); *G06T 2207/30016* (2013.01)

(58) Field of Classification Search
None
See application file for complete search history.

(56) References Cited

U.S. PATENT DOCUMENTS

| 6,526,305 | B1 |   | 2/2003 | Mori |   |
|---|---|---|---|---|---|
| 7,657,071 | B2 | * | 2/2010 | Bartesaghi et al. | 382/128 |
| 7,881,878 | B2 | * | 2/2011 | Burrus et al. | 702/28 |
| 8,731,256 | B2 | * | 5/2014 | Mori et al. | 382/128 |

(Continued)

FOREIGN PATENT DOCUMENTS

| WO | 2009-088965 A1 | 7/2009 |
| WO | WO 2011106821 A1 * | 9/2011 |

OTHER PUBLICATIONS

International Search Report and Written Opinion under date of mailing of Dec. 7, 2011 in connection with PCT/US2011/029964.

*Primary Examiner* — Bhavesh Mehta
*Assistant Examiner* — Oneal R Mistry
(74) *Attorney, Agent, or Firm* — Quarles & Brady, LLP

(57) ABSTRACT

A coordinate system particular to a subject's tissue, such as a subject's brain, is provided. Furthermore, a system and method for multi-dimensional, interrelated tractography is provided. Images of the subject are acquired that include diffusion information and tracts and/or vectors potentially associated with tracts are determined therefrom. With respect to the coordinate system, this information is used along with an basis that the tracts and/or vectors generally conform to a substantially orthogonal grid, such that white matter tissue fibers are arranged as one of substantially parallel or substantially orthogonal to other fibers. This coordinate system may be provided to a user along with reconstructed images, or may be used to process images. Similarly, in multi-dimensional, interrelated tractography, a new predictive ability and new metrics are provided along with an improved ability to reconstructed or process images.

34 Claims, 16 Drawing Sheets

(56) References Cited

U.S. PATENT DOCUMENTS

| | | |
|---|---|---|
| 2003/0216634 A1 | 11/2003 | van Muiswinkel et al. |
| 2005/0101857 A1 | 5/2005 | Masutani et al. |
| 2008/0122440 A1* | 5/2008 | Sakai et al. ............ 324/309 |
| 2009/0232374 A1* | 9/2009 | Simon ..................... 382/131 |
| 2010/0244834 A1* | 9/2010 | Mori et al. ............ 324/310 |
| 2011/0262021 A1* | 10/2011 | Liu ......................... 382/131 |
| 2012/0172705 A1* | 7/2012 | Jain et al. ............. 600/410 |
| 2013/0009959 A1* | 1/2013 | Calamante ....... G01R 33/56341 345/428 |
| 2015/0055845 A1* | 2/2015 | Jensen ................ G06T 7/0081 382/131 |

* cited by examiner

SYSTEMS AND METHODS FOR IMPROVED TRACTOGRAPHIC PROCESSING

CROSS-REFERENCE TO RELATED APPLICATIONS

This application represents the national stage entry of PCT International Application No. PCT/US2011/029964 filed Mar. 25, 2011. which claims the benefit of U.S. Provisional Patent Application Ser. No. 61/340,980, filed on Mar. 25, 2010, and entitled "System, Apparatus and Method for Imaging," and U.S. Provisional Patent Application Ser. No. 61/422,313, filed on Dec. 13, 2010, and entitled "System, Apparatus and Method for Imagine", both of which are incorporated herein by reference in their entirety for all purposes.

STATEMENT REGARDING FEDERALLY SPONSORED RESEARCH

N/A.

BACKGROUND OF THE INVENTION

The field of the invention is systems and methods for medical imaging. More particularly, the invention relates to systems and methods for improving tractography and tractographic processes, for example, by producing and using a subject-specific coordinate system that conforms to a tissue of interest or considering the interrelation of tracts during tractography or processes related to tractography.

Understanding brain connectivity on a global scale is likely a prerequisite to understanding brain function. Whereas studies in animals with tract-tracers have identified individual pathways and their topology as complex networks, studies of the geometric organization of connectivity in the context of brain evolution, development, plasticity, neural coding, and large-scale cerebral specialization have suggested much simpler organization. The need to synthesize these disparate viewpoints is long recognized and has prompted technical innovation and basic discovery. That is, the research and development to date has been able to capture small and explain small portions of the overall brain architecture, but there has been a clear desire to determine a single view to brain. However, while progress has been achieved outside the forebrain, no single picture yet describes both the geometric and topologic character of cerebral connectivity. Particularly, it has been significantly difficult to accurately map cerebral pathways in an anatomical context, or anatomical relations between pathways in a single brain.

The large-scale structure of the primate cerebral connectome—the totality of fiber pathways of the cerebral white matter—has been elusive. In the late 19th to early 20th century investigations of connectional neuroanatomy using traditional dissection and microscopy uncovered basic principles of large-scale brain organization and development. By the mid 20th century, these methods were supplanted by more precise and reproducible methods of fiber tracing. The success of the fiber tracing approach, and its emphasis on point-to-point connectivity, however, tended to remove from view questions about the organization of the brain at larger scales. The three-dimensional relations between fiber pathways are difficult to discover with fiber tracing techniques, and the presumption is often made that these relations are of secondary importance.

Recently, magnetic resonance imaging ("MRI") methods, such as diffusion MRI, have been developed to map major fiber pathways in a single brain. Diffusion MRI now affords a means by which to map the connectional anatomy of a single brain in its entirety, and to do so rapidly, three-dimensionally, nondestructively, and noninvasively. In the development of this technology, a key advance was the recognition of the problem of ubiquitous fiber crossings in the brain. The difficulty fiber crossings posed for early diffusion tensor imaging ("DTI") mapping of fiber pathways helped lead to the development of methods for accurately resolving fiber crossings, such as diffusion spectrum imaging ("DSI"), Q-Ball imaging, q-space imaging ("QSI"), and other related techniques. While these methods provide an ability to resolve complex fiber architecture at each location, the quantitation of complex fiber architecture and of diffusion beyond the tensor remains challenging, and an active area of research.

SUMMARY OF THE INVENTION

It is an aspect of the present invention to provide a method for producing an image of a subject by acquiring image data of a brain of the subject that includes white matter tissue and reconstructing an image of the subject that depicts the white matter tissue from said acquired image data. Coordinate system information may be produced by correlating the white matter tissue in the reconstructed image with a coordinate system in which the white matter tissue is arranged in a substantially orthogonal grid. The reconstructed image and the produced coordinate system information are then provided to a user for further use. Also, improved tractogrpahy and tractographic processing may be performed by determining and using interrelation information between the tracts and potential tracts.

It is another aspect of the invention to provide a method for guiding processing of an image of a subject by acquiring with a magnetic resonance imaging system, image data from a subject that includes white matter tissue containing white matter fibers, the image data being sensitized to diffusion. From this acquired image data, an image of the subject that depicts the white matter tissue is reconstructed. Using this reconstructed image, a coordinate system particular to the subject and in which different white matter fibers are arranged one of substantially parallel to each other and substantially orthogonal to each other is defined. This coordinate system is used to process an image of the subject to produce a metric indicative of a characteristic of the subject.

It is yet another aspect of the invention to provide a non-transient computer readable storage medium having stored thereon instructions that when carried out by a processor direct the processor to perform a method that acquires image data of a brain of the subject that includes white matter tissue, the acquired image data reflecting diffusion information about the white matter tissue. From the acquired image data, a coordinate system particular to the subject in which the white matter tissue is arranged in a substantially orthogonal grid is defined. The defined coordinate system is then correlated with the image data.

It is still another aspect of the invention to provide a method for determining white matter fiber paths in a brain of a subject using medical imaging data is disclosed that includes acquiring image data of the subject that includes information about the white matter tissue in the brain of the subject including diffusion information. The method also includes determining a first vector from the diffusion information potentially corresponding to a portion of a first white matter fiber path formed in the white matter tissue in the brain of the subject and determining a second vector from the diffusion information potentially corresponding to a portion of a second white matter fiber path formed in the white matter tissue in the brain of the subject. The method further includes performing an interrelated tractography procedure using the diffusion data, the first vector, and the second vector and considering relative components of the first vector and the second vector to one another to evaluate a likelihood of correspondence to the first white matter fiber path and second white matter fiber path. The method includes building a representation of the first white matter fiber path and the second white matter fiber path formed in the white matter tissue in the brain of the subject.

It is yet another aspect of the invention to provide a method for determining white matter fiber paths in a brain of a subject using medical imaging data is disclosed that includes acquiring image data of the subject that includes information about the white matter tissue in the brain of the subject including diffusion information. The method also includes determining a first vector from the diffusion information potentially corresponding to a portion of a first white matter fiber path formed in the white matter tissue in the brain of the subject and determining a second vector from the diffusion information potentially corresponding to a portion of a second white matter fiber path formed in the white matter tissue in the brain of the subject. The method further includes determining a third vector from the diffusion information potentially corresponding to a portion of a third white matter fiber path formed in the white matter tissue in the brain of the subject and assigning a principal direction of the first vector, the second vector, and the third vector corresponding to one of longitudinal, transverse, and dorsoventral orientations in the brain of the subject. The method includes building a representation of the first white matter fiber path, the second white matter fiber path, and the third white matter fiber path considering relative components of the first vector, the second vector, and the third vector and the assigned principal direction to one another.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

In general, the present invention relates to systems and methods for producing and using a conformal coordinate system of a tissue of interest in a subject from diffusion information related to the tissue of interest that is acquired with magnetic resonance imaging ("MRI"). A subject may include an animal subject including humans and other mammals, and an exemplary tissue of interest may be brain tissue, including white matter tissue. The coordinate system is generally structured such that tissue pathways, such as white matter fiber pathways, are organized into a two-dimensional or three-dimensional grid. These grids are substantially orthogonal in as much as the pathways contained within the grid and arranged with respect to the coordinate system intersect at substantially right angles. The present invention recognizes that this coordinate system and the underlying "grid structure" may be standardized across different subjects. A coordinate system that is representative of such "grid structures" is herein referred to as a "grid structure coordinate system." Exemplary grid structure coordinate systems, systems and methods for defining such coordinate systems, and systems and methods for using such coordinate systems are described below in detail. First, a brief description of an exemplary MRI system and data acquisition scheme for use with the present invention are provided.

MRI System

Figure 1:
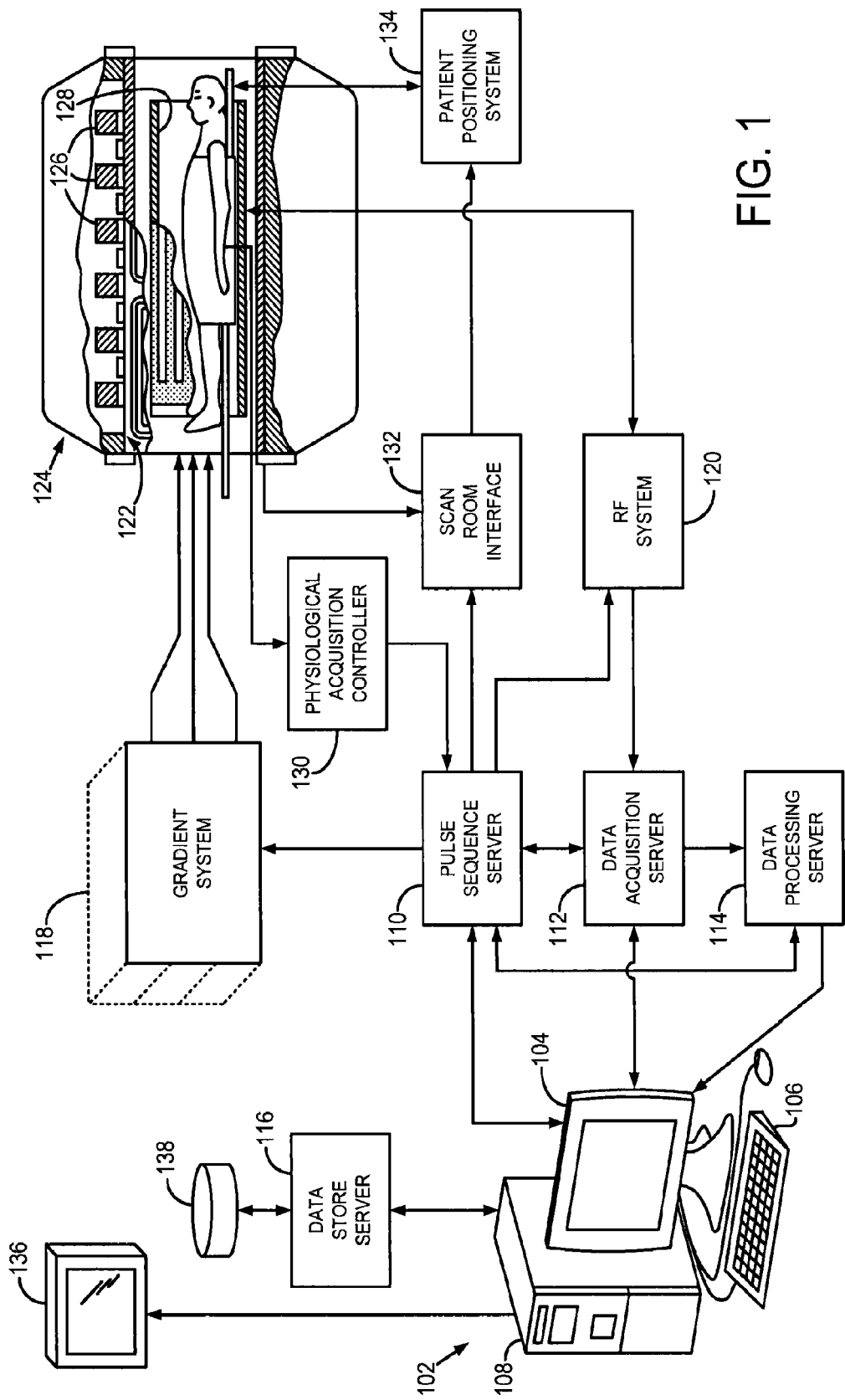
FIG. 1 is a block diagram of an exemplary magnetic resonance imaging ("MRI") system that employs the present invention.

Referring particularly now to FIG. 1, an exemplary MRI system 100 for use with the present invention is illustrated. The MRI system 100 includes a workstation 102 having a display 104 and a keyboard 106. The workstation 102 includes a processor 108, such as a commercially available programmable machine running a commercially available operating system. The workstation 102 provides the operator interface that enables scan prescriptions to be entered into the MRI system 100. The workstation 102 is coupled to four servers: a pulse sequence server 110; a data acquisition server 112; a data processing server 114, and a data store server 116. The workstation 102 and each server 110, 112, 114 and 116 are connected to communicate with each other.

The pulse sequence server 110 functions in response to instructions downloaded from the workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding MR signals. The gradient coil assembly 122 forms part of a magnet assembly 124 that includes a polarizing magnet 126 and a whole-body RF coil 128.

RF excitation waveforms are applied to the RF coil 128, or a separate local coil (not shown in FIG. 1), by the RF system 120 to perform the prescribed magnetic resonance pulse sequence. Responsive MR signals detected by the RF coil 128, or a separate local coil (not shown in FIG. 1), are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays (not shown in FIG. 1).

The RF system 120 also includes one or more RF receiver channels. Each RF receiver channel includes an RF amplifier that amplifies the MR signal received by the coil 128 to which it is connected, and a detector that detects and digitizes the I and Q quadrature components of the received MR signal. The magnitude of the received MR signal may thus be determined at any sampled point by the square root of the sum of the squares of the I and Q components:

$$M = \sqrt{I^2 + Q^2} \tag{1}$$

and the phase of the received MR signal may also be determined:

$$\phi = \tan^{-1}\left(\frac{Q}{I}\right). \tag{2}$$

The pulse sequence server 110 also optionally receives patient data from a physiological acquisition controller 130. The controller 130 receives signals from a number of different sensors connected to the patient, such as electrocardiograph ("ECG") signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110. Also, navigator signals may be acquired during a scan and used to adjust the operating parameters of the RF system 120 or the gradient system 118, or to control the view order in which k-space is sampled. The data acquisition server 112 may also be employed to process MR signals used to detect the arrival of contrast agent in a magnetic resonance angiography ("MRA") scan. In all these examples, the data acquisition server 112 acquires MR data and processes it in real-time to produce information that is used to control the scan.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 114 are conveyed back to the workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

Data Acquisition

Example Pulse Sequence

To acquire image data that can be used to produce or define a coordinate system in accordance with embodiments of the invention, diffusion imaging schemes such as diffusion spectrum imaging ("DSI"), Q-Ball imaging, q-space imaging ("QSI"), and diffusion tensor imaging ("DTI") may be used. It will be appreciated by those skilled in the art that for these imaging schemes several different pulse sequences may be implemented to acquire image data. One such exemplary pulse sequence is described below.

Figure 2:
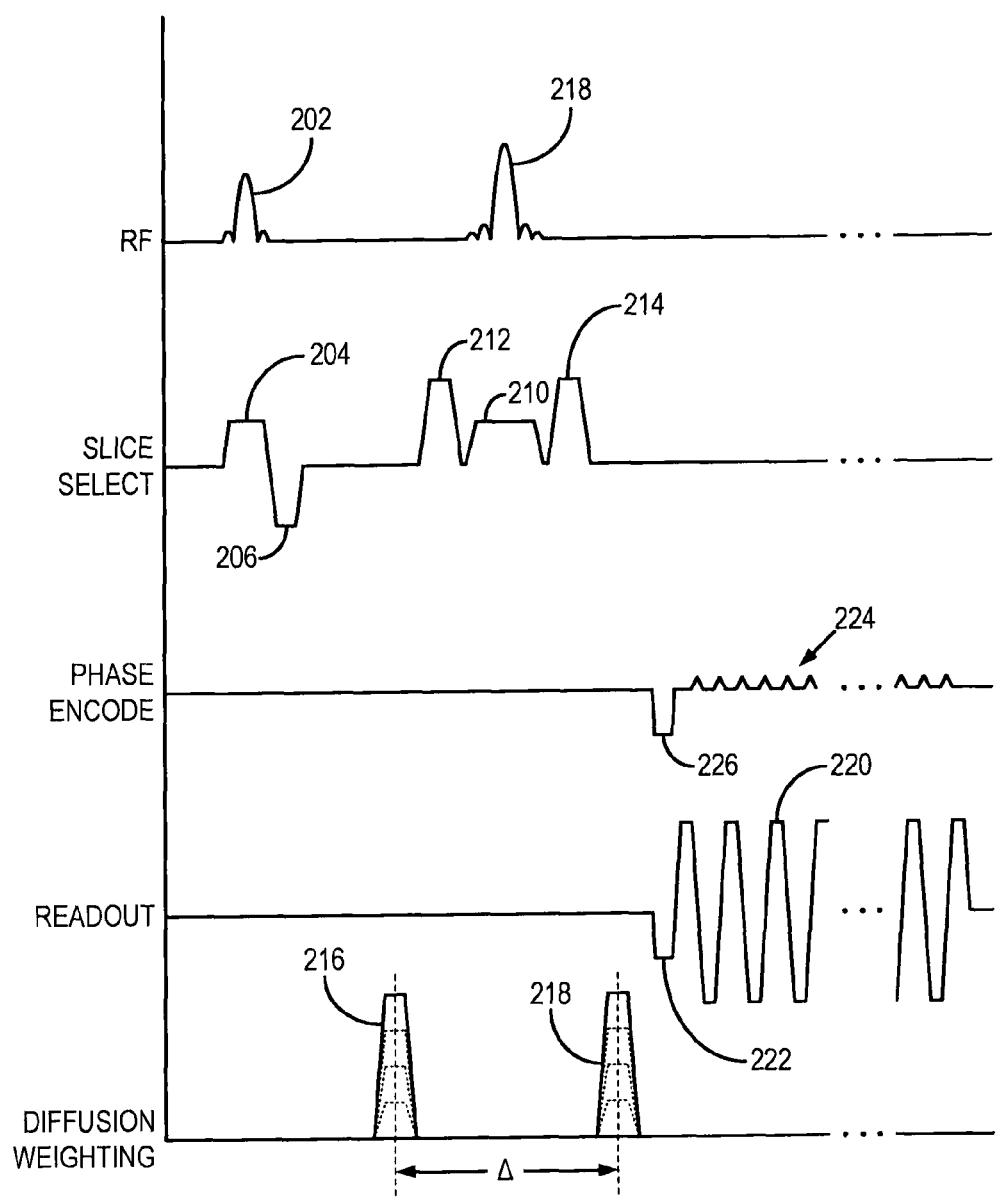
FIG. 2 is a graphic illustration of an exemplary diffusion weighted imaging ("DWI") spin-echo, echo planar imaging ("EPI") pulse sequence for directing the MRI system of FIG. 1 to acquire diffusion data.

By way of example, a spin-echo, echo planar imaging ("EPI") pulse sequence for acquiring image data with an MRI system is illustrated in FIG. 2. While this exemplary pulse sequence is illustrated here, it will be appreciated by those skilled in the art that other pulse sequences can be employed to perform diffusion data acquisition, such as gradient-echo based sequences and other spin-echo based sequences, including, for example, twice refocused spin echo ("TRSE") EPI sequences. Additionally, pulse sequences that employ hybrid two dimensional echo-planar and 3DFT spatial encoding may be used.

The spin-echo EPI sequence begins with an RF excitation pulse 202 that is played out in the presence of a slice selective gradient 204. To mitigate signal losses resulting from phase dispersions produced by the slice selective gradient 204, a rephasing lobe 206 is applied after the slice selective gradient 204. Next, a rephasing RF pulse 208 is applied in the presence of another slice selective gradient 210. In order to substantially reduce unwanted phase dispersions, a first crusher gradient 212 bridges the slice selective gradient 210 with a second crusher gradient 214. The slice-selective gradient 210 and crusher gradients 212 and 214 are further bridged by a first and second diffusion weighting gradient, 216 and 218, respectively. These diffusion weighting gradients 216 and 218 are equal in size, that is, their areas are equal. The diffusion weighting gradients 216 and 218, while shown on a separate "diffusion weighting" gradient axis, are in fact produced through the application of diffusion weighting gradient lobes along each of the slice-encoding, phase-encoding, and frequency-encoding gradient directions. By changing the amplitudes and other characteristics of the diffusion weighting gradient lobes, the acquired echo signals can be weighted for diffusion occurring along any arbitrary direction. For example, when the diffusion weighting gradients 216 and 218 are composed solely of gradient lobes applied along the $G_z$ gradient axis, then the acquired echo signals will be weighted for diffusion occurring along the z-direction. For another example, however, if the diffusion weighting gradients 216 and 218 are composed of gradient lobes applied along both the $G_x$ and $G_y$ gradient axes, then the echo signals will be weighted for diffusion occurring in the x-y plane along a direction defined by the relative amplitudes of the gradient lobes.

Diffusion weighting of the acquired echo signals is provided when spins undergo random Brownian motion, or diffusion, during the time interval, $\Delta$, spanned between the application of the first and second diffusion gradients 216 and 218, respectively. The first diffusion weighted gradient 216 dephases the spins in the imaging volume, whereas the second diffusion weighted gradient 218 acts to rephase the spins by an equal amount. When spins undergo random diffusive motion during this time interval, however, their phases are not properly rephased by the second diffusion gradient 218. This phase difference results in a signal attenuation related to the diffusion occurring along the direction prescribed by the diffusion weighting gradients 216 and 218. The more diffusion that occurs, the more signal attenuation that results.

Image data is acquired by sampling a series of diffusion weighted spin echo signals in the presence of an alternating readout gradient 220. The alternating readout gradient is preceded by the application of a pre-winding gradient 222 that acts to move the first sampling point along the frequency-encoding, or readout, direction by a distance $\Delta k_x$ in k-space. Spatial encoding of the echo signals along a phase-encoding direction is performed by a series of phase encoding gradient "blips" 224, which are each played out in between the successive signals readouts such that each echo signal is separately phase encoded. The phase encoding gradient blips 224 are preceded by the application of a pre-winding gradient 226 that acts to move the first sampling point along the phase-encoding direction a distance $\Delta k_y$ in k-space. Together, the pre-winding gradients 222 and 226 serve to begin the sampling of k-space at a defined k-space location $(k_x,k_y)$.

In an exemplary implementation, a DSI imaging scheme with the following parameters may be used: a cubic lattice of 515 diffusion gradient values, peak diffusion sensitivity (b-value) of $4\times10^4$ seconds per millimeter-squared (s/mm$^2$), diffusion gradient times of $\Delta=22$ milliseconds and $\delta=16$ milliseconds, and peak gradient intensity of 380 milli-Tesla per meter. Image matrices may be 80×80×80 to 140×140×140 with isotopic three-dimensional resolution of 300-500 micrometers.

General Description

When used to examine the brain, the grid structure coordinate system is useful to describe, simplify, and compare other images of the brain, and can be implemented to reliably compare one brain to another. The produced coordinate system may also be useful for creating representations and measures of brain connectivity that are, when compared to traditional representations and measures, easy to understand, easy to measure, and easy to compare between individuals. While the description provided herein makes reference to examples of determining a coordinate system that conforms to the brain and white matter tissue contained therein, it will be appreciated by those skilled in the art that the coordinate system may also be produced for other tissues, for example, such as skeletal muscle, smooth muscle, and cardiac muscle.

The present invention recognizes that the typical structure of cerebral white matter, when properly construed, is that of a biaxial or tri-axial grid of mutually orthogonal, and potentially interwoven, fiber paths. Thus, the present invention recognizes that white matter tissue can be understood to conform to a substantially orthogonal grid structure. To uncover this conformity, however, a grid structure coordinate system may be defined so that the white matter fibers paths may be mapped into that coordinate system. Such a grid structure coordinate system may be defined, for example, to include three principal axes: a longitudinal axis, a transverse axis, and a dorsoventral axis. While the grid structure coordinate system may be defined over these three principal axes, in some portions of the brain the grid structure coordinate system may be a two-dimensional coordinate system that is defined by only two of the aforementioned principal axes.

Generally, a grid structure coordinate system can be defined over a portion of a subject's brain, such as the cerebrum, the cerebellum, the pons, the medulla, or portions thereof, such as the telencephalon, the diencephalon, and the mesencephalon, or portions thereof, such as an anatomical region-of-interest in the telencephalon, and so on. By defining grid structure coordinate systems over these smaller portions of the brain, ensembles of grid structure coordinate systems over a single brain can be defined. These ensembles may be connected together or may be analyzed, for example, by measuring their mutual coherence. Furthermore, the number of grid structure coordinate systems contained in an ensemble may be allowed to grow infinitely large, thereby resulting in a set of probabilistic coordinates.

A coordinate system that conforms to an underlying biaxial or tri-axial grid structure may be defined, as will be described below in detail, using diffusion information, such as diffusion vector information, obtained from diffusion weighted MR images. The diffusion information can be analyzed to determine the principal direction of white matter fiber paths in the brain. For those fiber paths extending predominantly in the anterior-posterior ("AP") direction, the fiber paths are identified as extending in the "longitudinal" direction of the defined coordinate system; for those fiber paths extending predominantly in the left-right ("LR") direction, the fiber paths are identified as extending in the "transverse" direction of the defined coordinate system; and for those fiber paths extending predominantly in the superior-inferior ("SI") direction, the fiber paths are identified as extending in the "dorsoventral" direction in the defined coordinate system.

Figure 3:
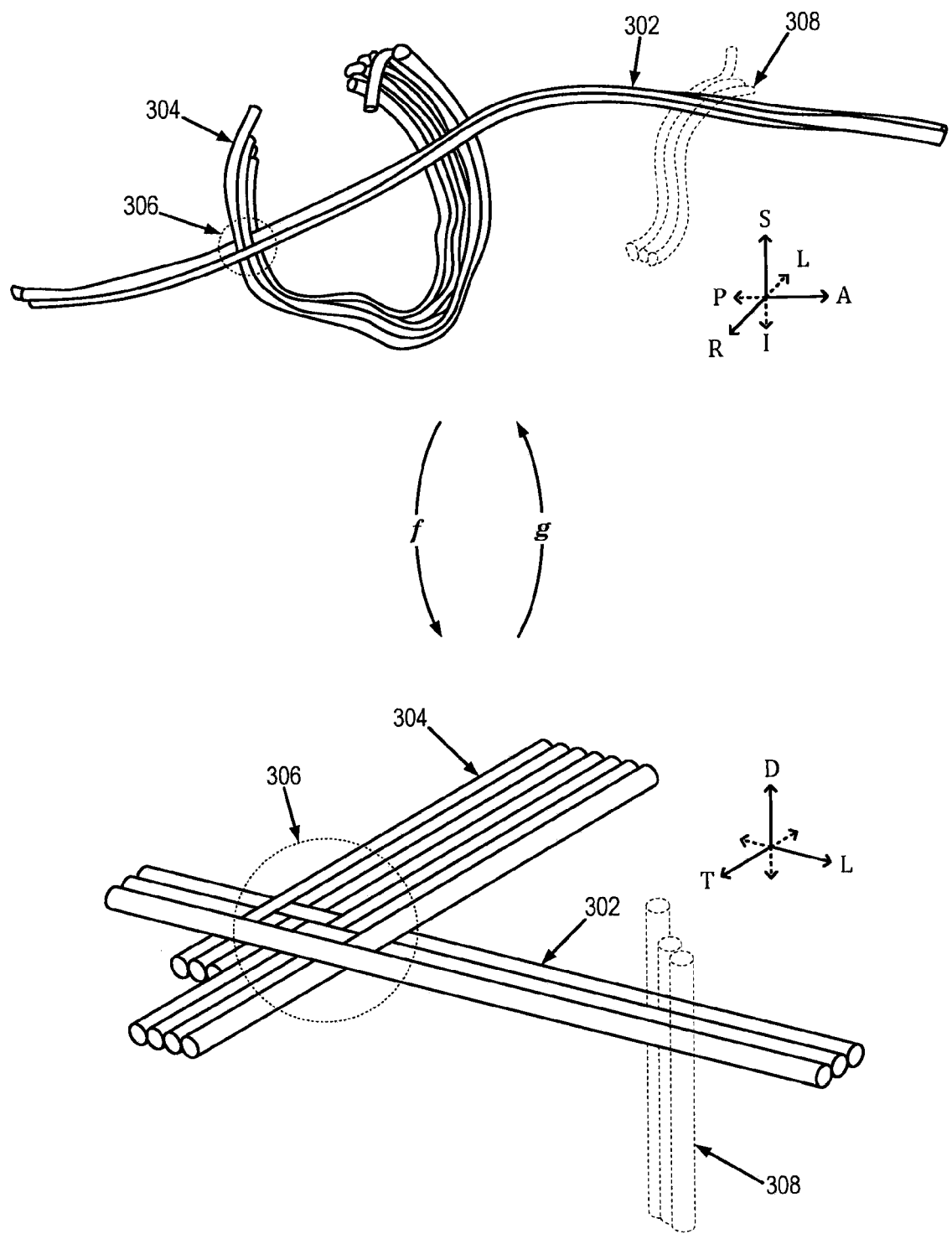
FIG. 3 is a pictorial representation of an exemplary superior longitudinal fasciculus I fiber path and corpus callosum fiber path that cross in a volume-of-interest and a grid structure coordinate system mapped therebetween in accordance with embodiments of the present invention.

Referring to FIG. 3, and by way of example, an exemplary fiber path for a superior longitudinal fasciculus I ("SLF I") 302 as it crosses the corpus callosum 304 in a volume-of-interest 306 is illustrated. The SLF I 302 predominantly extends in the AP direction and the corpus callosum 304 extends predominantly in the LR direction while curving about the AP axis, generally, in the SI direction. In accordance with the present invention, a grid structure coordinate system for the SLF I 302 and corpus callosum 304 fiber path neighborhoods may be advantageously defined by analyzing these fiber paths. Because the SLF I 302 fiber path extends predominantly in the AP direction, the SLF I 302 fiber path is assigned as extending along the longitudinal direction in the grid structure coordinate system. Similarly, while the corpus callosum 304 curves in the SI direction, the predominant extension of the corpus callosum 304 fiber path is in the LR direction; thus, the corpus callosum 304 fiber path is assigned as extending along the transverse direction in the grid structure coordinate system.

In accordance with the present invention, the fiber paths can be mapped into and transformed to and from the grid structure coordinate system. This bidirectional transform is illustrated using the representative transfer function, f( ) and inverse transfer function, g( ). The transfer function and inverse transfer functions will be described below.

By way of the transfer function, f( ) the SLF I 302 fiber paths and corpus callosum 304 fiber paths are illustrated as having been mapped into the grid structure coordinate system. Thus, using the grid structure coordinate system of the present invention, the fiber paths incident on the volume-of-interest 306 include two substantially orthogonal components: longitudinal paths within the SLF I and transverse paths within the corpus callosum.

Preliminarily, several observations regarding the grid structure coordinate system of the present invention are of note. First, the present invention recognizes that the curved paths of each directional component are substantially parallel. That is, the component pathways are similar in orientation, generally, do not interweave with each other, and their relative orderings remain. Second, the present invention recognizes that pairs of transverse or longitudinal paths will not generally cross more than once. Third, the present invention recognizes that fiber pathways are substantially aligned with the cardinal body axes near the mid-sagittal plane, and that they continuously curve away from these axes with distance while maintaining their orthogonal inter-relationships. Thus, though curved, the grid structure in accordance with the present invention appears simple, strict, and continuously related to the transverse and longitudinal axes of the central nervous system and of the body. Thus, the present invention recognizes that even though cerebral pathways may deviate from a single grid path, in doing so the pathways still closely adhere to another grid orientation. The biaxial structure of path neighborhoods is not limited to particular two-dimensional surfaces, but is present throughout three-dimensional volumes. The pathways within each sheet in a stack of sheets are parallel to their counterpart paths in sheets of different depths in the stack.

Pathways of two different crossing families lie within the same extended, curved two-dimensional surface. By the existence theorem for partial differential equations, the likelihood of this phenomenon is expected to be significantly low. The discovery that in the cerebral white matter, the mutual intersections of families of transverse paths in three dimensions generally define a family of parallel sheets is therefore real and non-trivial. Crossed direction fields in three dimensions, such as smooth plane fields, do not generally specify well-defined curved two-dimensional surfaces, but do so when they satisfy an auxiliary condition, such as that their mutual twist is everywhere zero. This condition is specified, for example, by the Deahna-Clebsch-Frobenius theorem. The mutual intersections of fiber paths through multiple seed volumes form closed rectangles, and not open three-dimensional rectangular spirals that are overwhelmingly expected for generic orientation fields.

As some exemplary illustrations detail below, these concepts can be extended into a variety of useful extrapolations and extend or enhance a wide variety of clinical applications. For example, still referring to FIG. 3, knowing that the curved paths of each directional component are substantially parallel, that pairs of transverse or longitudinal paths will not generally cross more than once, and that fiber pathways are substantially aligned with the cardinal body axes near the mid-sagittal plane, a variety of predictions and/or constraints on predictions or analysis can be made. For example, in either domain, one can use the identification of the SLF I 302 fiber paths and corpus callosum 304 fiber paths and a basis to predict and/or constrain the prediction or identification of additional fiber paths 308. Specifically, using the identification of the SLF I 302 fiber paths and corpus callosum 304 fiber paths and/or the transform of these fiber paths 302, 304 onto the grid structure, one can predict and/or constrain the prediction or identification of additional fiber paths 308 to be substantially parallel (in the case of the corpus callosum 304) or perpendicular (in the case of the SLF I 302) and extend substantially aligned with the cardinal body axes. As will be illustrated below, this ability to predict and/or constrain prediction or analysis provides a highly-powerful tool for analyzing the human brain in a myriad of clinical applications.

General Illustrations

Figure 4:
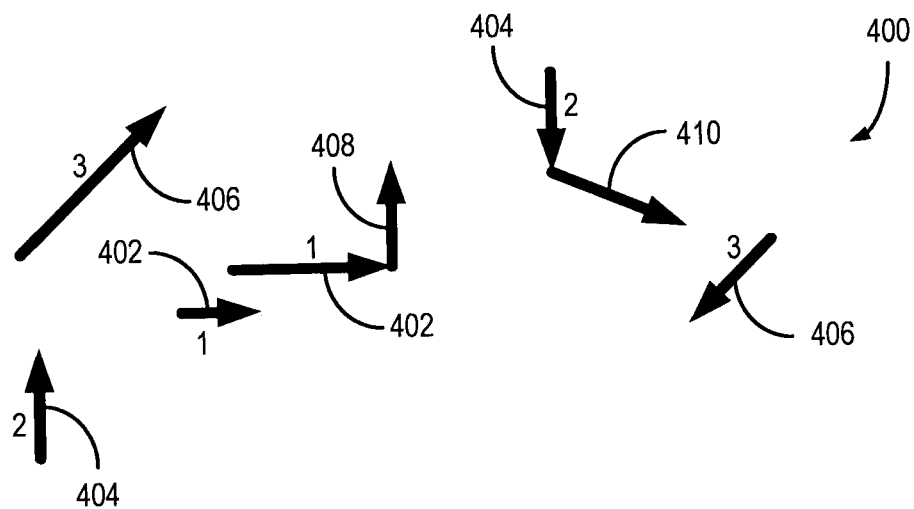
FIG. 4 is a graphic representation of a plurality of vectors determined using a tractography-type process and processed in accordance with the present invention.

Referring now to FIG. 4, in a basic application, one may identify fiber paths in the brain, such as those described above with respect to FIG. 3, using vectors, generally designated 400. More particularly, these vectors 400, when correlated in the image domain, such as when beginning a fiber tractograpy application, may represent portions of fiber tracts. In the illustration, these vectors 400 appear to be independent and not interrelated. However, using the principles described above to constrain an analysis of these vectors 400, it can be assumed that the curved paths of each directional component are substantially parallel, that pairs of transverse or longitudinal component will not generally cross more than once, and that vectors are substantially aligned with the cardinal body. With these constraints, the vectors 400 can be analyzed and designated, for example, using a marker that identifies the vector as extending along a given component of the above-described, grid coordinate system. Specifically, the vectors 400 can be assigned designations, in the illustrated example, numbers, that identifies the vector as extending along a given component of the above-described, grid coordinate system. Vectors extending along longitudinal direction are assigned a "1" marker 402, those extending in the transverse direction are assigned a "2" marker 404, and those extending in the dorsoventral direction are assigned a "3" marker 406.

As will be described, this ability to constrain or resolve a preliminary assignment of the vectors representing potential fiber tracts provides a powerful tool for enhancing many traditional brain analyses and providing new mechanisms for analyzing the brain. For example, as will be described in further detail, one can perform multi-dimensional, interrelated tractography. Specifically, using the diffusion data acquired from a subject, a first vector 402, and a second vector 404, the relative components of the first vector 402 and the second vector 404 to one another can be evaluated to determine a likelihood of correspondence to white matter fiber paths. For example, starting with the first vector 402, further tractography can be performed to determine an extension 408 from the first vector potentially corresponding to additional portions of a white matter fiber path. Comparing the relative components of the extension 408 from the first vector to the other vectors 402, 404, 406, one can evaluate a likelihood of correspondence to a white matter fiber path. Specifically, it can be determined that the extension 408 of the first vector 402 yielded through tractographic processes extends generally perpendicular to the first vector 402 and third vector 406 and parallel to the second vector 404. By considering the relative components of the extension 408 from the first vector to the other vectors 402, 404, 406, one can determine that the extension 408 has a relatively high likelihood of correspondence to a white matter fiber path because it is substantially parallel or perpendicular to the vectors 402, 404, 406. That is, it can readily be assigned a assigned a "2" marker. On the other hand, a extension 410 of the second vector 404, when compared to the other vectors 402, 404, 406, deviates from the expected parallel/perpendicular/substantially orthogonal orientation and, thus, cannot be readily assigned any of the aforementioned markers. However, it can also serve as important information. For example, it may indicate that the extension 410, which may be derived through a traditional imaging and tractography process, such as DTI, may not correctly correspond with an actual fiber path. For example, the traditional imaging and tractography process, such as DTI, may have erroneously resolved a fiber crossing. Accordingly, as will be described, the extension 410 may be disregarded as part of an interrelated tractography process in favor of a more properly resolved vector extension when compared to the other vectors 402, 404, 406, or as described hereafter, a grid structure coordinate system. Additionally, the deviation of the extension from the expected/predicted path may indicate a deformity of the fiber paths, which also has substantial clinical value.

Accordingly, this process of comparing the relative components of the extension 408 from the first vector to the other vectors 402, 404, 406 is referred to as interrelated tractography because, unlike traditional tractograpy procedures, it considers the relation of a given vector/extension to other vectors/extensions. Furthermore, it may be referred to as multi-dimensional interrelated tractography because it considers the relative components, including magnitude and direction, of other potential fiber tracts.

Vector Field Method for Defining Grid Structure Coordinate System

Figure 5:
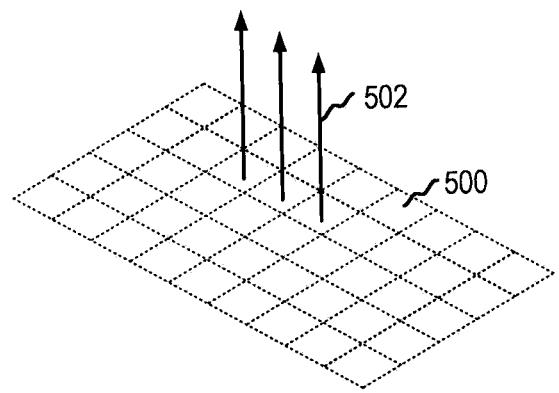
FIG. 5 is a graphic representation of a sheet of fiber tracts and orthogonal vectors determined in accordance with the present invention.

The above-described vector/assignment analysis can be extended to build more sophisticated analysis and modeling tools. Referring to FIG. 5, a given plurality of vectors extending substantially parallel and perpendicular, for example, those extending along the longitudinal direction and those extending along the transverse direction, can be used to form a function describing a plane 500 and vectors 502 extending perpendicular therefrom.

As described above, this procedure includes classifying each potential pathway represented as a vector as one of longitudinal, transverse, and dorsoventral, such as by assigning numerical markers. One can then calculate scalar potentials representative of the principal axes (longitudinal, transverse, and dorsoventral), including a longitudinal scalar potential, $\phi(l)$, a transverse scalar potential, $\phi(t)$, and a dorsoventral scalar potential, $\phi(d)$. For example, a vector in a white matter fiber path calculated using tractography may define a location along that fiber path as a vector, v, having the following form:

$$v=(v_x,v_y,v_z) \quad (3);$$

where $v_x=v(x)$, $v_y=v(y)$, and $v_z=v(z)$ are the vector components of the diffusion vector field location, v, along the x-direction, y-direction, and z-direction, respectively. These vector components can be related to the desired scalar potentials as follows:

$$\nabla\phi(l)=c(y)v(y) \quad (4);$$

$$\nabla\phi(t)=c(x)v(x) \quad (5);$$

and $$\nabla\phi(d)=c(z)v(z) \quad (6);$$

where c(x), c(y), and c(z) are constants. The result of solving, or approximating, Eqns. Error! Reference source not found.—Error! Reference source not found. is to determine those locations where the scalar potentials $\phi(l)$, $\phi(t)$, and $\phi(d)$ point along the directions of the vector field components v(y), v(x), and v(z), where the vector field, v, is defined. Interpolation may be used between locations in the vector field, v, to calculate the scalar potentials at a location between those where the vector field, v, is defined.

Figure 6:
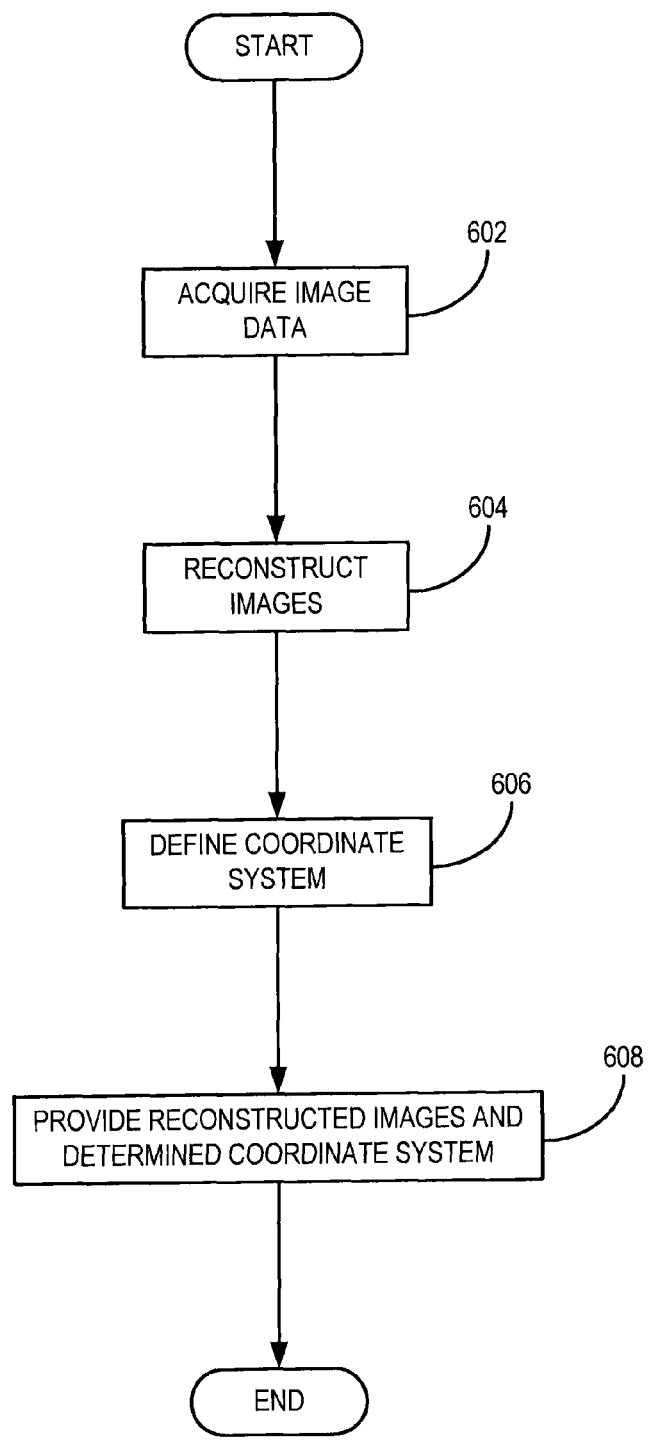
FIG. 6 is a flowchart setting forth the steps of an exemplary method for producing a coordinate system that is conformal to a substantially orthogonal three-dimensional grid structure and to diffusion information obtained with an MRI system.

Referring now to FIG. 6, a flowchart setting forth the steps of an exemplary method for producing a coordinate system pertaining to a subject's neuroanatomy, such as white matter tissue, is illustrated. The method begins with the acquisition of image data from a subject using an MRI system, as indicated at step 602. As described above, image data is acquired with a diffusion imaging scheme, such as DSI, Q-Ball imaging, DTI, or other such techniques, using a pulse sequence such as, for example, the one illustrated in FIG. 2. From the acquired image data, images of the subject are reconstructed, as indicated at step 604. Because these images were produced using a diffusion imaging scheme, they are indicative of diffusion occurring within tissues in the subject. For example, images of the brain are indicative of diffusion occurring within brain tissues, such as gray matter and white matter tissue. Using the reconstructed images, a grid structure coordinate system may be defined, as indicated at step 606. Exemplary methods for defining the grid structure coordinate system are described below in detail. Following the generation of the grid structure coordinate system, the reconstructed images of the subject and the grid structure coordinate system may be provided to a user, as indicated at step 608, so that they can be used for subsequent applications.

Figure 7A:
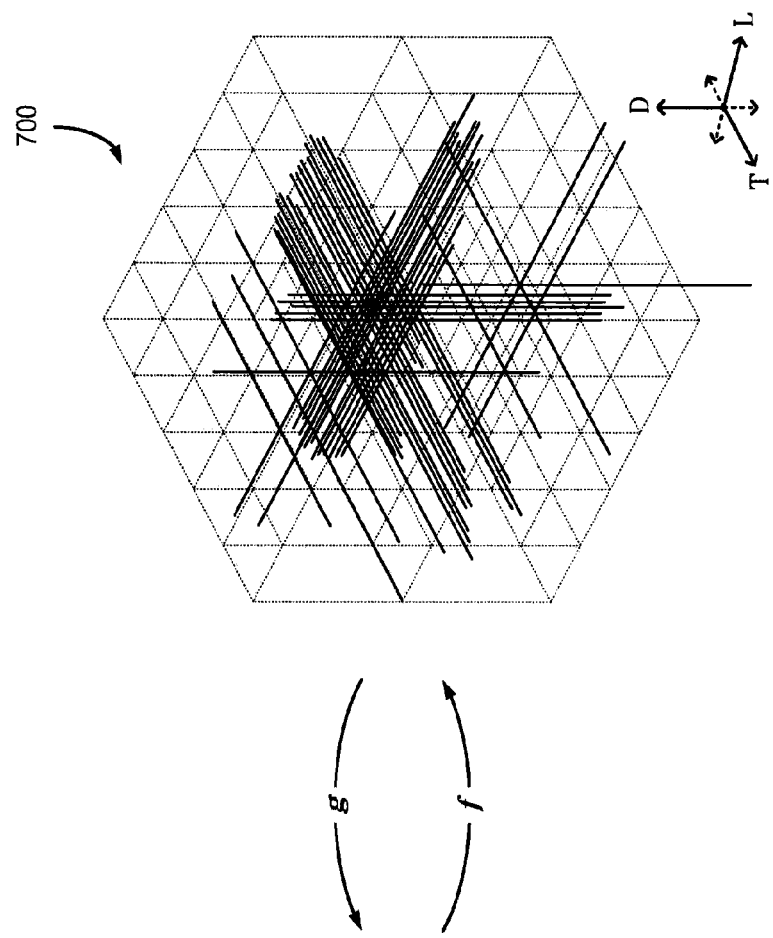
FIG. 7A is pictorial representation of an exemplary fiber bundle and a three dimensional grid structure coordinate system mapped therebetween in accordance with the present invention.
Figure 7A:
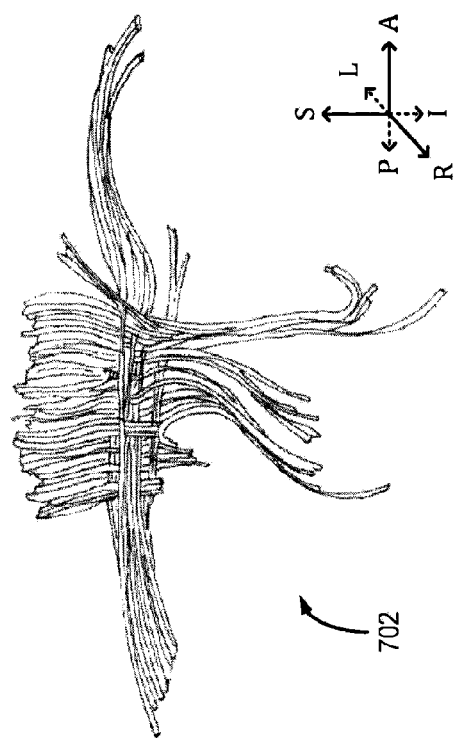
Figure 7B:
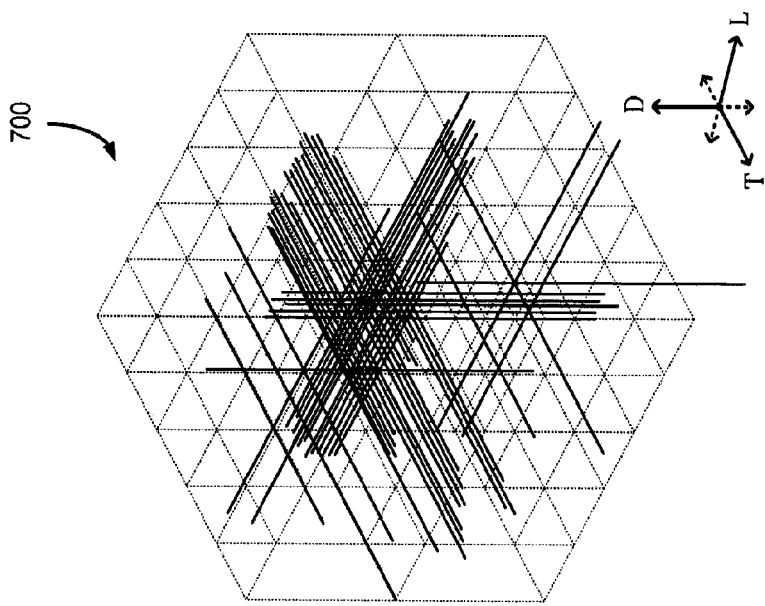
FIG. 7B is pictorial representation of an exemplary brain anatomy and a three dimensional grid structure coordinate system mapped therebetween in accordance with the present invention.
Figure 7B:
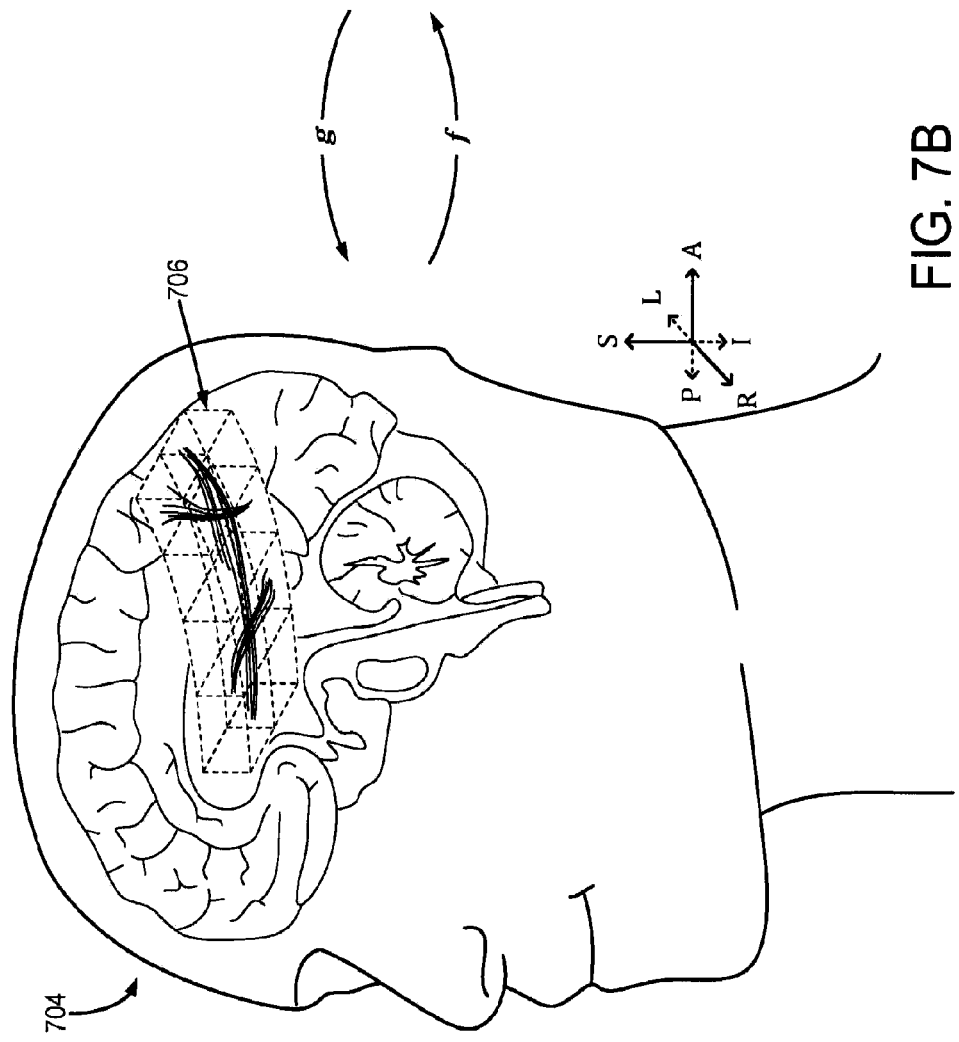
Figure 8:
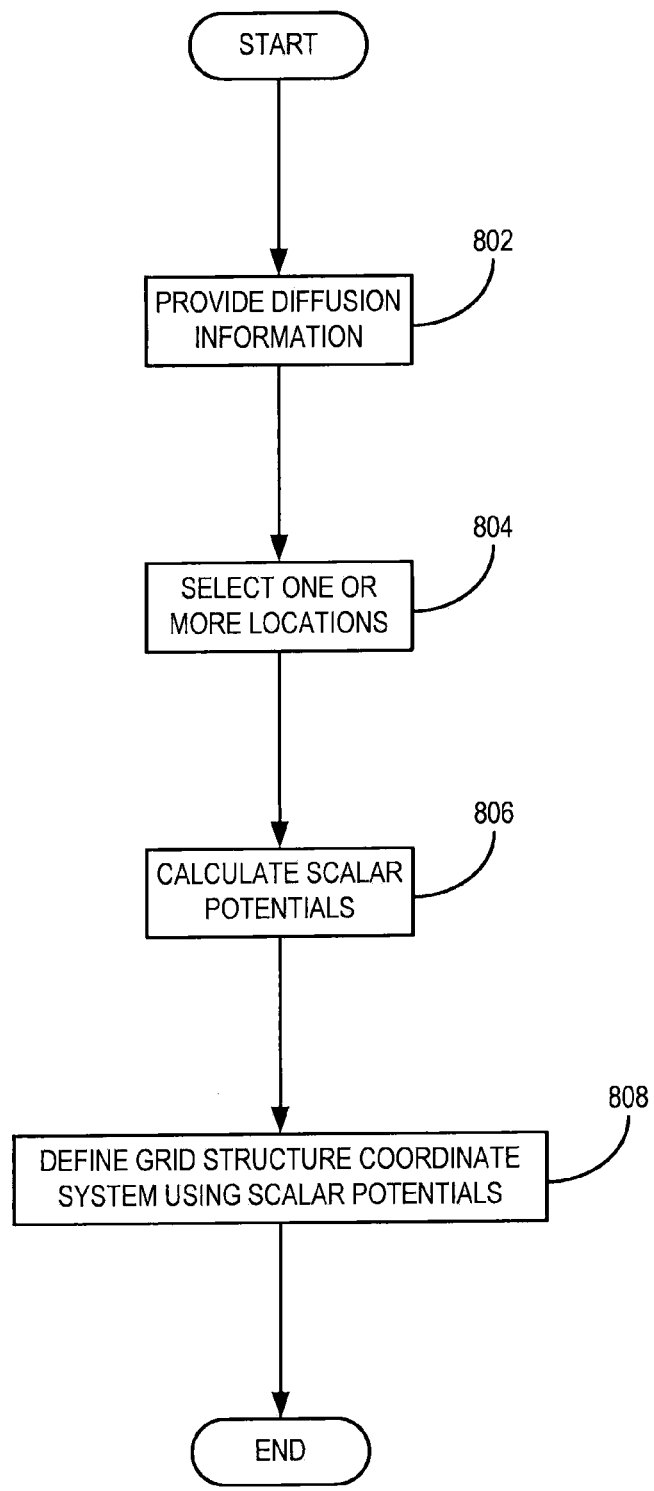
FIG. 8 is a flowchart setting forth the steps of an exemplary method for producing, or defining, a grid structure coordinate system using diffusion information contained in a vector field that describes tissue pathways, such as white matter tissue fiber paths.

Referring to FIGS. 7A, 7B, and 8, the above-described concepts can be utilized to form a method for producing, or defining, a grid structure coordinate system 700 using diffusion information contained in a vector field that describes diffusion occurring in tissue pathways, such as white matter tissue fiber paths 702, as shown in FIG. 7A. More generally, as shown in FIG. 7B, a grid structure coordinate system 700 may be mapped onto brain anatomy 704 in general, and vice versa. For illustrative purposes, a portion 706 of the grid structure coordinate system 700 is shown overlaid with the brain anatomy 704 to show aspects of the transformation that occurs when mapping between the grid structure coordinate system 700 and the brain anatomy 704. An exemplary method for defining a grid structure coordinate system using vector field information begins by first providing diffusion vector field information, as indicated at step 802. This diffusion information may be provided by performing tractography on the reconstructed images that depict diffusion in the subject, and such tractography may be performed, for example, using path integration or streamline tractography techniques. Alternatively, however, diffusion information can be obtained from the reconstructed images. For example, vector field information pertaining to diffusion can be obtained from diffusion tensors or orientation distribution functions ("ODFs") calculated from the reconstructed images.

The provided diffusion information is processed to define the grid structure coordinate system. One or more points in the provided diffusion information are selected, as indicated at step 804, and the vector field information at the one or more points is utilized to perform multi-dimensional, interrelated tractography. Specifically, as described above, using the diffusion data, a first vector, and a second vector, the relative components of the first vector and the second vector to one another are evaluated to determine a likelihood of correspondence to white matter fiber paths. In one implementation, this may be extended by calculating scalar potentials that define the grid structure coordinate system, as indicated at step 806. For example, Eqns. Error! Reference source not found.— Error! Reference source not found. may be solved using approximation methods to calculate the scalar potentials. By constraining the scalar potentials to be nonzero along one principal direction (e.g., longitudinal direction for the $\phi(l)$ scalar potential) and substantially zero along the directions orthogonal to the principal direction (e.g., transverse and dorsoventral directions for the $\phi(l)$ scalar potential), the grid structure coordinate system can be defined with respect to the calculated scalar potentials, as indicated at step 808.

When fiber paths have already been calculated by tractography, the fiber paths may be assigned to one of a longitudinal, transverse, and dorsoventral direction, in a manner such as described above with respect to FIG. 4, for example, using the scalar potential fields calculated at point associated with that fiber path. In addition, orientation information, that is, whether the fiber path extends along the positive or negative longitudinal, transverse, or dorsoventral direction, is preserved and also be assigned to the fiber path.

Topology Method for Defining Grid Structure Coordinate System

Figure 9:
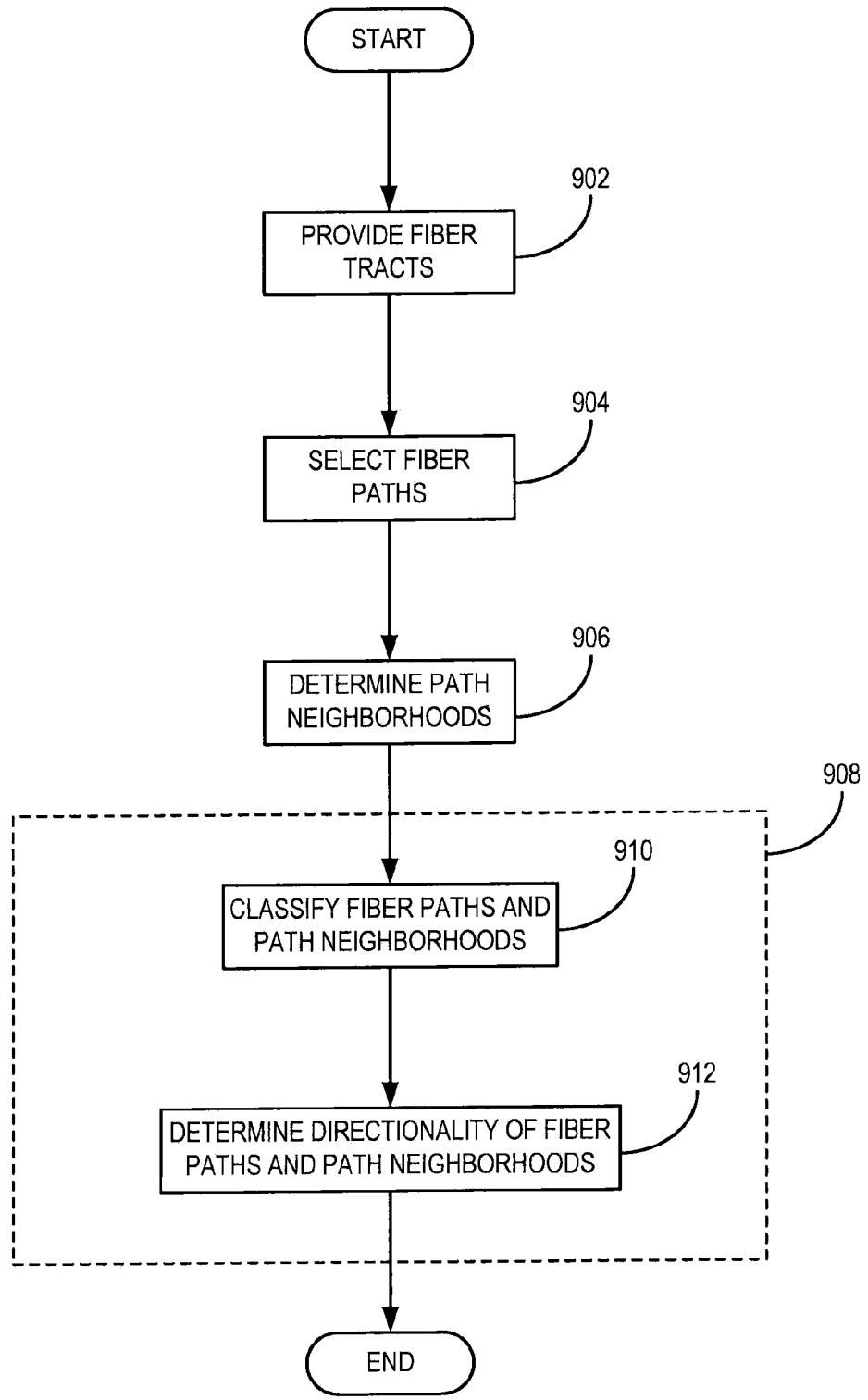
FIG. 9 is a flowchart setting forth the steps of an exemplary method for producing, or defining, a grid structure coordinate system using topological properties of tissue pathways, such as white matter tissue fiber paths.

Referring now to FIG. 9, a flowchart setting forth the steps of an exemplary method for producing, or defining, a grid structure coordinate system using topological properties of tissue pathways, such as white matter tissue fiber paths, is illustrated. Generally, this procedure includes classifying each pathway as one of longitudinal, transverse, and dorsoventral. White matter fiber tracts, such as those determined or calculated using tractography, are provided, as indicated at step 902. From these white matter fiber tracts, one or more fiber paths are selected for processing, as indicated at step 904. Using the selected paths, path neighborhoods are determined throughout the subject's brain, or a portion thereof, as indicated at step 906. For any given path, the set of all other paths that approach the given path to within a distance of, for example, one voxel is computed. Such paths are referred to as being "adjacent," and the set of all paths that are adjacent to a selected set of paths is referred to as the "neighborhood" of those selected paths. This adjacency includes as special cases both tangency and the crossing of paths. Adjacency represents a simple and neutral probe of the relational structure of the set of pathways, being equivalent to the definition of a topology on the space of paths. Thus, a topology of the fiber pathways in the brain is defined on path space using this adjacency.

Having identified the fiber paths and determined the path neighborhoods within the subject's brain, or the portion thereof, a coordinate system pertaining to the subject's neuroanatomy is determined, as indicated generally at 908. To produce a grid structure coordinate system, the paths adjacent a selected path are first classified as one of functionally parallel; part of the same fiber system; or functionally crossing, intersecting, or perpendicular, as indicated at step 910. Two remote paths are determined to be functionally parallel when intermediate paths spaced between the two remote paths are parallel to the remote paths. Thus, a transitive property of functionally parallel pathways is used. When two paths are not functionally parallel, they are determined to be functionally perpendicular. As noted above, the fiber paths are identified as belonging to one of a transverse, longitudinal, or dorsoventral principal coordinate direction. Fiber coordinates and fiber grid relations are used to identify this directionality of the fiber paths, as indicated at step 912. Fibers adjacent to a selected fiber may be decomposed into tangent (parallel) and crossing (perpendicular) fiber groups. Such a process can be advantageously utilized in particular clinical applications, some of which are described below, or more generally as described above.

Method or Producing Fiber Sheet Conformal Coordinates

Figure 10:
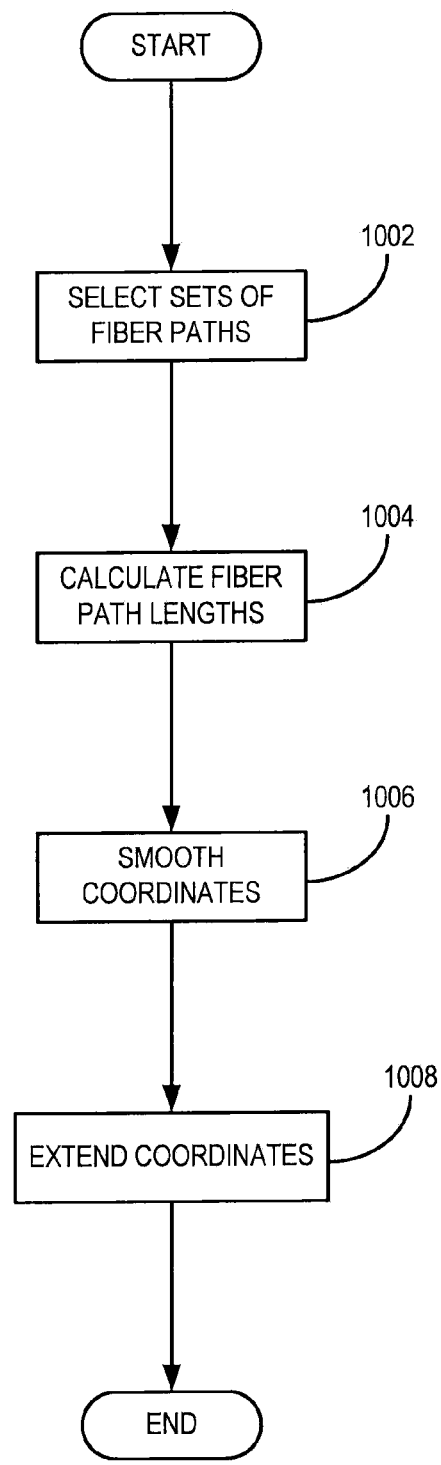
FIG. 10 is a flowchart setting forth the steps of an exemplary method for producing fiber sheet conformal coordinates.

Referring now to FIG. 10, a flowchart setting forth the steps of an exemplary method for producing fiber sheet conformal coordinates, such as referred to with respect to FIG. 5, is illustrated. A sheet of fibers may be produced from a set of fibers crossing a selected fiber. Likewise, a sheet of fibers may be produced from a set of fibers that mutually cross two selected fibers. Generally, fiber sheet conformal coordinates can be produced, given two sets of crossing paths, by defining a coordinate $\{x,y\}$, where x is a path distance measured alone one set of paths and y is a distance measured along the other. Thus, the method begins by selecting sets of fiber paths, as indicated at step 1002. The path lengths x and y are then measured along the selected sets of fiber paths, as indicated at step 1004, to define a local conformal coordinate. This local coordinate may then be smoothed and locally extended to three dimensions, as indicated at steps 1006 and 1008, respectively. Parallel fiber sheets can then be produced using the procedure described above, but extended to three dimensions. For example, the coordinates between parallel fibers and parallel sheets can be extended. Fiber volume conformal coordinates can then be produced as described above for sheet conformal coordinates, but expanded to three dimensions. For example, given overlapping fiber systems, the coordinates can be extended to cover their union. Fiber coordinates for the entire brain can be created in this manner by overlapping systems. These coordinates may be standardized in relation to standard anatomical landmarks, such as the brain mid-line, AC-PC line, or other observables such as the center of mass or moment of inertia of the brain. Such a process can be advantageously utilized in particular clinical applications, some of which are described below, or more generally as described above.

Having described methods for producing a grid structure coordinate system for white matter fiber pathways, several exemplary applications of such a coordinate system are now provided.

Comparison of Two or More Images

Figure 11A:
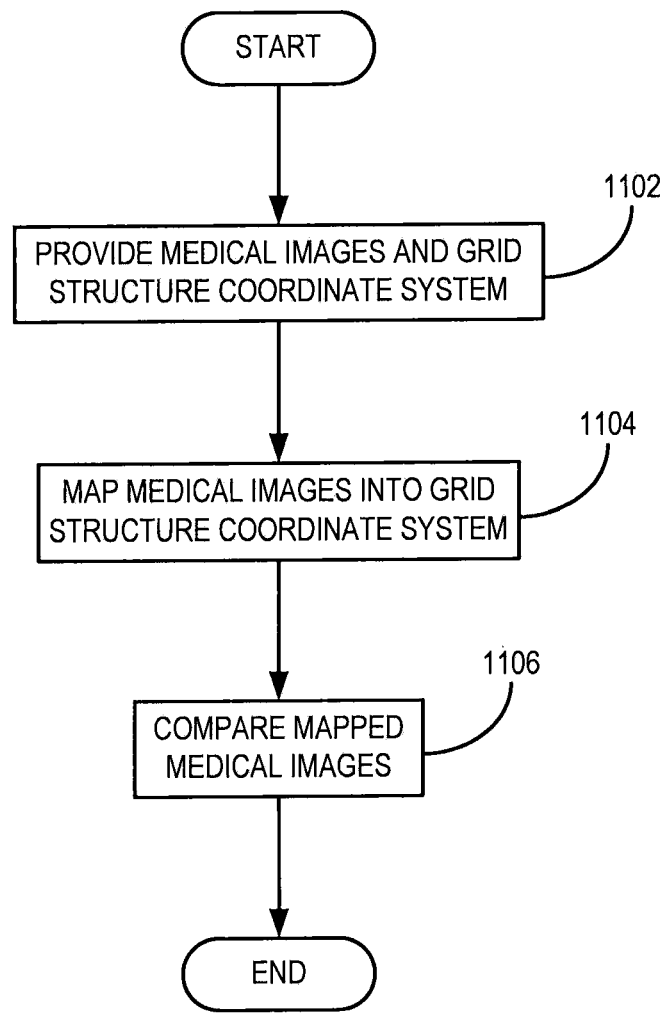
FIG. 11A is a flowchart setting forth the steps of an exemplary method for comparing medical images of two or more subjects using a grid structure coordinate system.

Referring now to FIG. 11A, a flowchart setting forth the steps of an exemplary method for comparing medical images of two or more subjects using a grid structure coordinate system is illustrated. That is, as explained above, the predictive nature of the present invention provides a mechanism through which sub-components of tractography, such as vectors or proposed extensions from vectors, can be evaluated with respect to one another. However, the evaluative uses of the present invention can likewise extend across multiple tractographic images. The method begins by providing medical images of the subjects and respective grid structure coordinate system information, as indicated at step 1102. Exemplary medical images that may be provided include magnetic resonance images such as T1-weighted, T2-weighted, diffusion weighted, functional, and contrast-enhanced or non-contrast-enhanced MR angiography images. Other exemplary medical images may include those acquired with x-ray imaging systems, including x-ray computed tomography ("CT") systems, and nuclear medicine imaging systems, including positron emission tomography ("PET") and single photon emission computed tomography ("SPECT") systems. Using the provided medical images and grid structure coordinate system information, each medical image can be mapped into the grid structure coordinate system, as indicated at step 1104, so that accurate and reliable comparisons can be made between the mapped medical images, as indicated at step 1106. Such comparisons may produce comparative information that serve as a metric indicative of characteristics of the subjects under examination.

By way of example, medical images, such as magnetic resonance images, of two or more brains from different subjects or multiple images of the same subject may be compared using known comparison and statistical methods after they have been mapped into the grid structure coordinate system. Using the example of comparing two brains from different subjects, because the brains share a common coordinate system that conforms to the subject's anatomy on one level, but describes a generalized anatomical relationship on another level, such comparisons can be made more reliably by mapping the relevant information to be compared into their respective coordinate systems before comparison.

Average Image

Figure 11B:
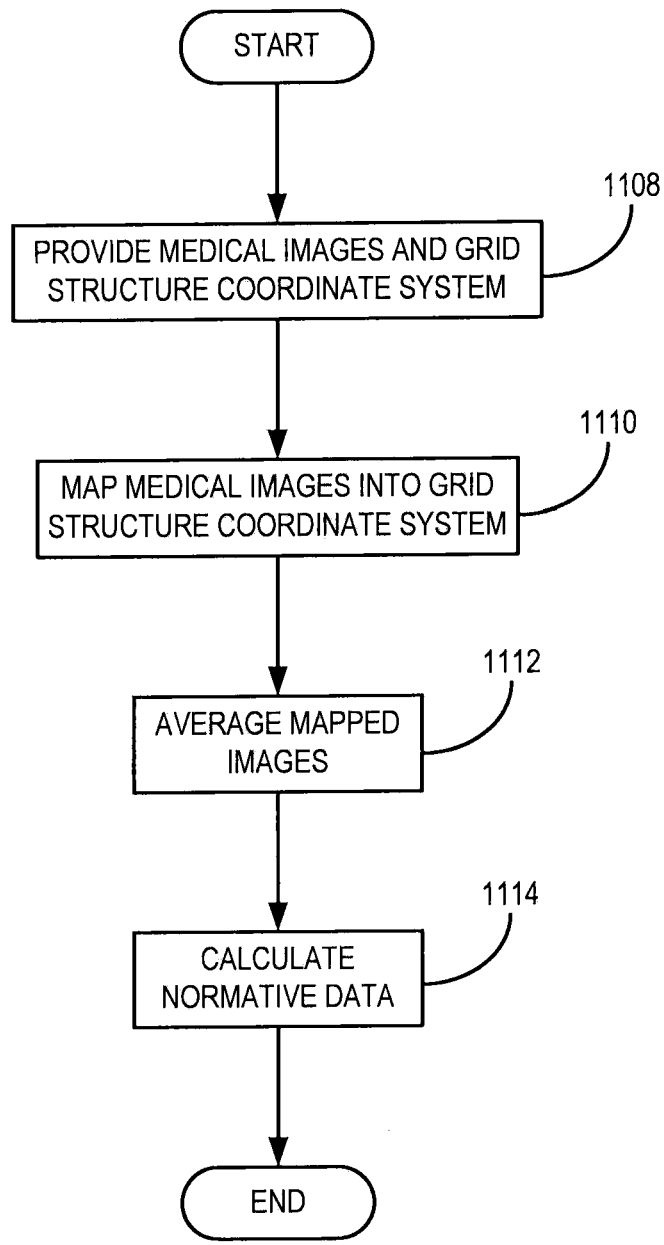
FIG. 11B is a flowchart setting forth the steps of an exemplary method for producing an average image from medical images obtained for multiple different subjects, and using a grid structure coordinate system.

Referring now to FIG. 11B, a flowchart setting forth the steps of an exemplary method for producing an average image from medical images obtained for multiple different subjects, and using a grid structure coordinate system, is illustrated. The method begins by providing medical images of the subjects and respective grid structure coordinate system information, as indicated at step 1108. Exemplary medical images that may be provided include magnetic resonance images such as T1-weighted, T2-weighted, diffusion weighted, functional, and contrast-enhanced or non-contrast-enhanced MR angiography images. Other exemplary medical images may include those acquired with x-ray imaging systems, including x-ray CT systems, and nuclear medicine imaging systems, including PET and SPECT systems.

Using the provided medical images and grid structure coordinate system information, each medical image can be mapped into the grid structure coordinate system, as indicated at step 1110. An "average" medical image can be created by averaging together the mapped medical images, as indicated at step 1112. Such an average image may be useful as a universal anatomical atlas that is based on the grid structure coordinate system, or for calculating normative data. For example, as indicated at step 1114, normative data for observables, such as average T1 or T2 values for particular tissue types, can be computed. Deviations from these normative data can then be measured on an individual basis and used as an informative diagnostic biomarker. In this manner, such normative data serves as a metric representative of a characteristic of a subject.

Connectivity

Figure 11C:
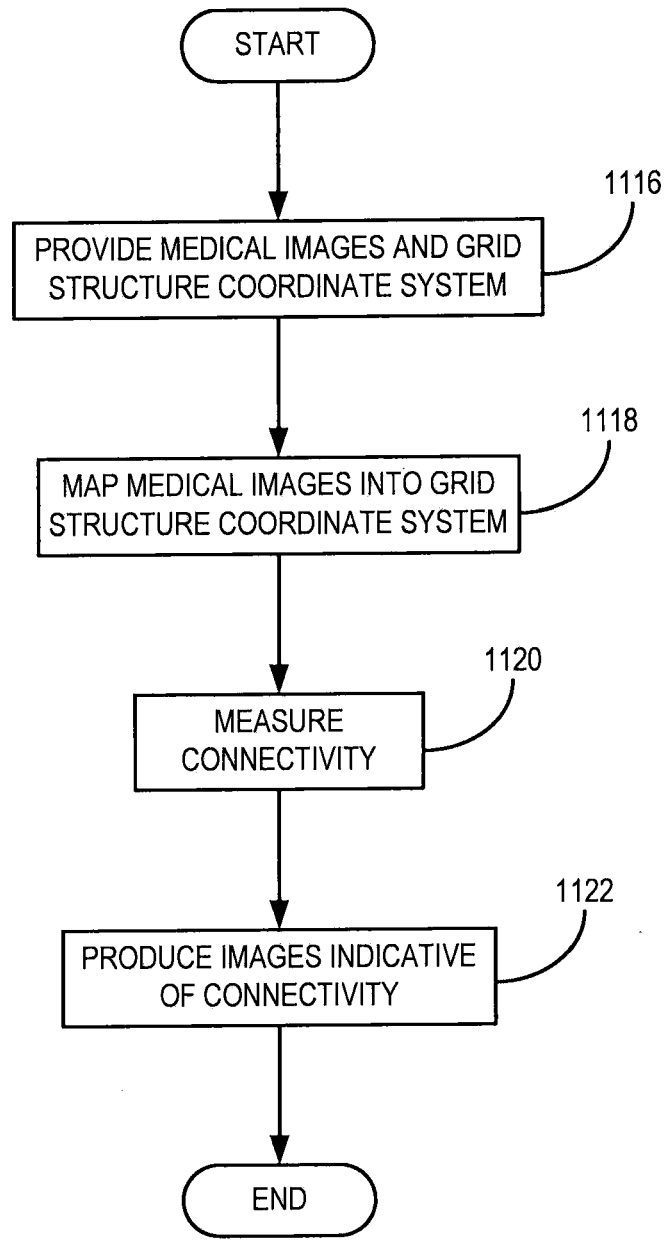
FIG. 11C is a flowchart setting forth the steps of an exemplary method for measuring and producing an image representative of the connectivity of fiber pathways in a subject's brain using a grid structure coordinate system.

Referring now to FIG. 11C, a flowchart setting forth the steps of an exemplary method for measuring and producing an image representative of the connectivity of fiber pathways in a subject's brain using a grid structure coordinate system is illustrated. The method begins by providing medical images of the subjects and respective grid structure coordinate system information, as indicated at step 1116. Exemplary medical images that may be provided include magnetic resonance images such as T1-weighted, T2-weighted, diffusion weighted, functional, and contrast-enhanced or non-contrast-enhanced MR angiography images. Other exemplary medical images may include those acquired with x-ray imaging systems, including x-ray CT systems, and nuclear medicine imaging systems, including PET and SPECT systems. Using the provided medical images and grid structure coordinate system information, each medical image can be mapped into the grid structure coordinate system, as indicated at step 1118

Connectivity of the brain can be described and measured using the produced grid structure coordinate system. For example, general connectivity can be measured between two or more longitudinal, transverse, and dorsoventral, or $\{l,t,d\}$, coordinates, and cortical connectivity may be measured between two longitudinal, transverse, or $\{l,t\}$, coordinates, as indicated at step 1120. This latter example may include the projection from three-dimensional $\{l,t,d\}$ coordinates to two-dimensional $\{l,t\}$ coordinates. Fiber path connectivity may also be measured by projecting each component onto itself. For example, longitudinal connectivity may be measured by producing a three-dimensional image that may specify at each point, for example, the projected longitudinal component, l', or the spatial path offset (path length), l-l'. The entire connectome may then be represented by three such images, one for each principal $\{l,t,d\}$ coordinate; thus, images representative of such fiber connectivity may be produced, as indicated at step 1122. Such images represent a metric that is indicative of a characteristic of the subject; for example, such a metric may represent the connectivity of fibers in the subject's brain.

Fiber Density Metric

Figure 11D:
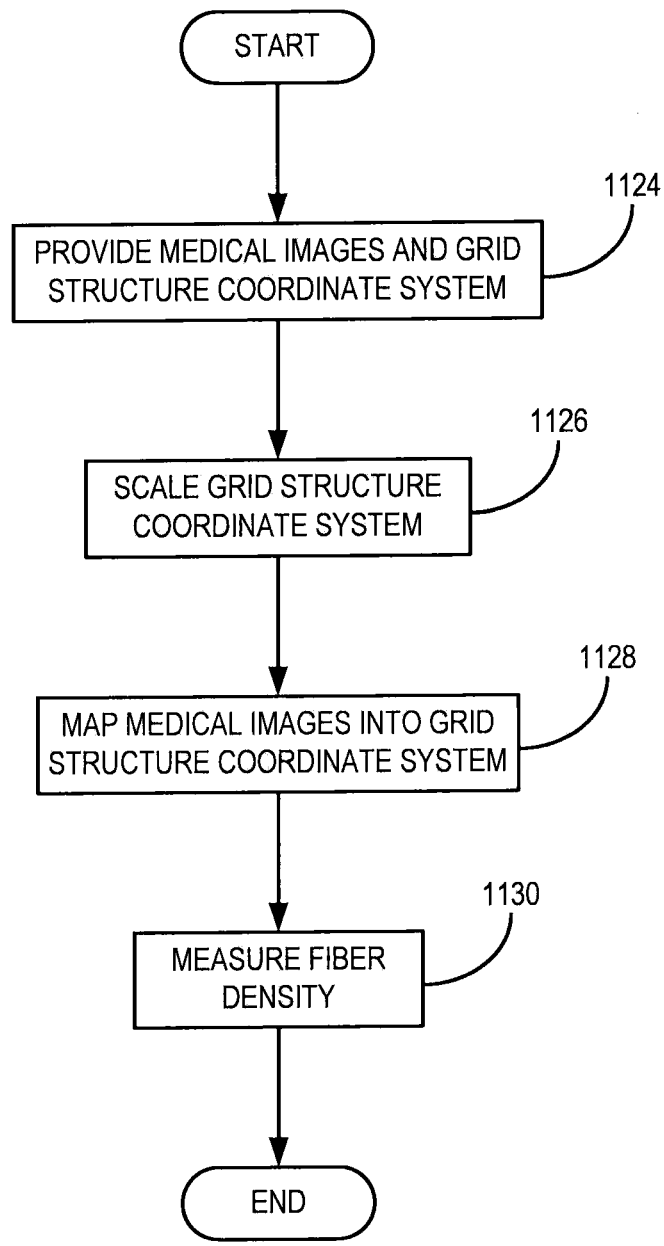
FIG. 11D is a flowchart setting forth the steps of an exemplary method for calculating a fiber density measure using a grid structure coordinate system.

Referring now to FIG. 11D, a flowchart setting forth the steps of an exemplary method for calculating a fiber density measure using a grid structure coordinate system is illustrated. The method begins by providing medical images of the subjects and respective grid structure coordinate system information, as indicated at step 1124. Exemplary medical images that may be provided include magnetic resonance images such as T1-weighted, T2-weighted, diffusion weighted, functional, and contrast-enhanced or non-contrast-enhanced MR angiography images. Other exemplary medical images may include those acquired with x-ray imaging systems, including x-ray CT systems, and nuclear medicine imaging systems, including PET and SPECT systems. The provided grid structure coordinate system is then scaled, or rescaled, as indicated at step 1126. For example, the coordinates can be scaled or rescaled to be representative of the total number of pathways over a particular distance in the grid structure coordinate system. Using the provided medical images and scaled grid structure coordinate system information, each medical image can be mapped into the grid structure coordinate system, as indicated at step 1128. The density of fibers in the subject can then be measured and normalized using the scaled grid structure coordinate system and mapped medical images, as indicated at step 1130. In this manner, a metric in the form of a normalized measure of fiber density can be provided across different subjects.

Coordinate System Accuracy

Figure 11E:
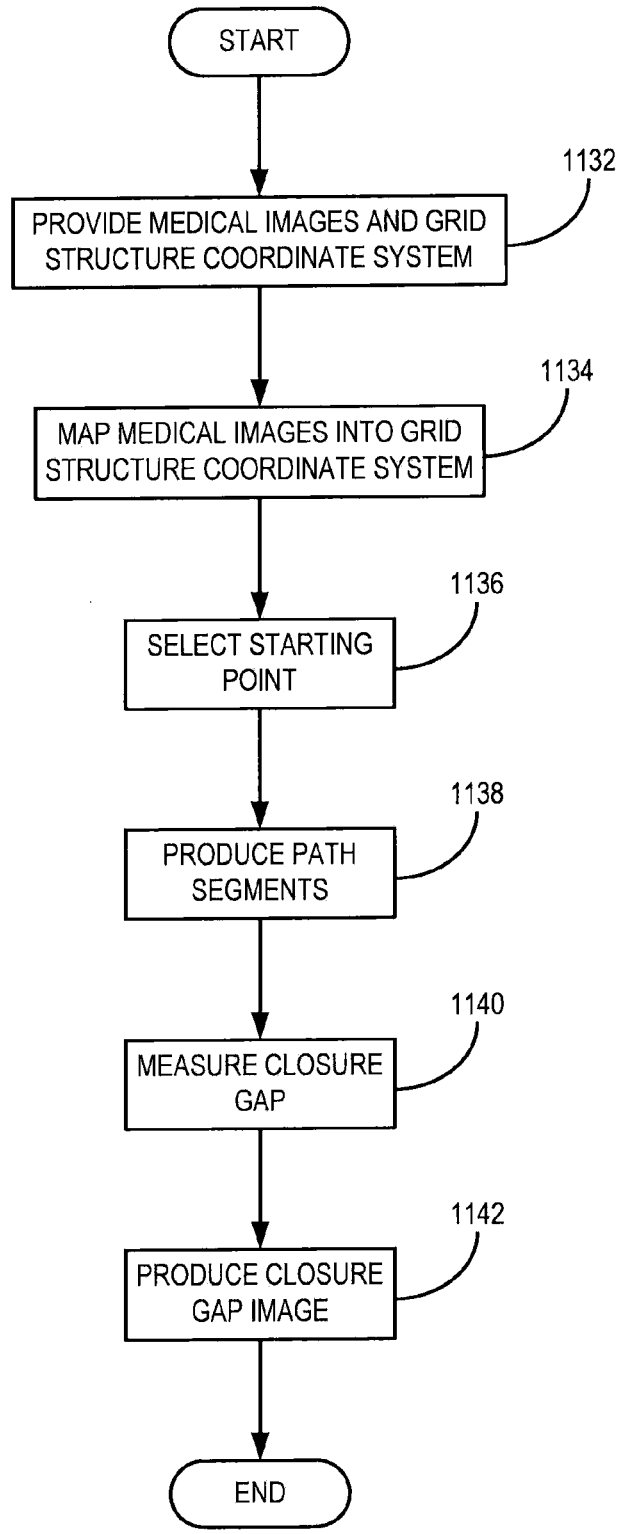
FIG. 11E is a flowchart setting forth the steps of an exemplary method for measuring the accuracy of a grid structure coordinate system.

Referring now to FIG. 11E, a flowchart setting forth the steps of an exemplary method for measuring the accuracy of a grid structure coordinate system is illustrated. The method begins by providing medical images of the subjects and respective grid structure coordinate system information, as indicated at step 1132. Exemplary medical images that may be provided include magnetic resonance images such as T1-weighted, T2-weighted, diffusion weighted, functional, and contrast-enhanced or non-contrast-enhanced MR angiography images. Other exemplary medical images may include those acquired with x-ray imaging systems, including x-ray CT systems, and nuclear medicine imaging systems, including PET and SPECT systems. Using the provided medical images and grid structure coordinate system information, each medical image can be mapped into the grid structure coordinate system, as indicated at step 1134.

The accuracy of the coordinate system itself can be assessed by, for example, computing a measure of the coordinate system, such as a so-called "Frobenius defect," or closure defect of the coordinates. In such a method, a starting point in a fiber pathway in the coordinate system is selected, as indicated at step 1136. From this starting point, a sequence of fiber segments is produced, as indicated at step 1138. These fiber segments are produced such that in a Cartesian coordinate system, they would form a closed polygon or curve. A vector across the final closure gap of this sequence of fiber segments is then measured, as indicated at step 1140. By way of example, consider four steps along coordinate directions "a" and "b":

$$\begin{cases} 0 \to a, \\ a \to (a+b), \\ (a+b) \to (a+b-a), \\ (a+b-a) \to (a+b-a-b) \end{cases} \quad (7)$$

The vector representation of the gap from the start to the finish in this example is given by:

$$g=(a+b-a-b) \quad (8).$$

These gap closure defects show the "singularities" in the paths of the brain. For any two coordinate directions, these closure defects can be computed at every point where both directions are defined. Thus, an "image" of the closure defects can be produced and displayed, as indicated at step 1142. Because this closure gap image represents a measure of a grid structure coordinate system that pertains to a particular subject, such closure gap measures are metrics indicative of a characteristic of a subject, such as the grid structure coordinate system defined with respect to the subject.

Method for Regression Analysis

Figure 11F:
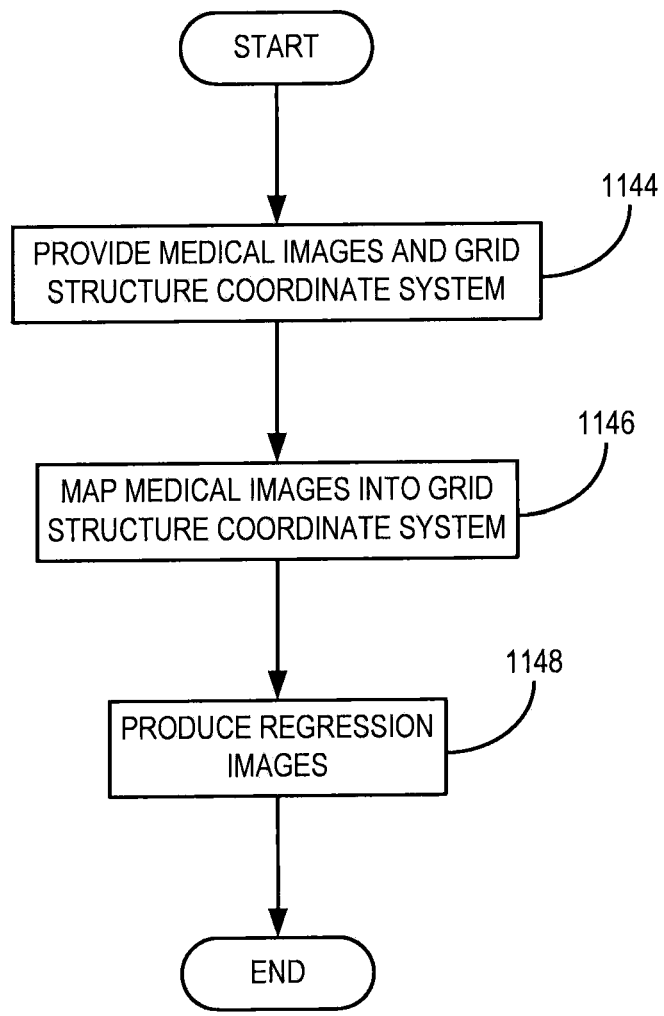
FIG. 11F is a flowchart setting forth the steps of an exemplary method for producing an image of a subject's anatomy, such as the subject's brain, at a different age of the subject using a grid structure coordinate system.

Referring now to FIG. 11F, a flowchart setting forth the steps of an exemplary method for producing an image of a subject's anatomy, such as the subject's brain, at a different age of the subject using a grid structure coordinate system is illustrated. The method begins by providing medical images of the subjects and respective grid structure coordinate system information, as indicated at step 1144. Exemplary medical images that may be provided include magnetic resonance images such as T1-weighted, T2-weighted, diffusion weighted, functional, and contrast-enhanced or non-contrast-enhanced MR angiography images. Other exemplary medical images may include those acquired with x-ray imaging systems, including x-ray CT systems, and nuclear medicine imaging systems, including PET and SPECT systems. Using the provided medical images and grid structure coordinate system information, each medical image can be mapped into the grid structure coordinate system, as indicated at step 1146. These mapped images can then be regressed to a different age of the subject using a model of tissue organization for the subject, as indicated at step 1148. In this manner, images of the subject's anatomy at different ages of the subject can be produced, thereby providing a metric of the subject's anatomical growth.

Thus, the present invention recognizes and defines herein a "grid structure" of cerebral white matter that indicates the presence of previously-unrecognized constraints on the geometry and topology of cerebral connectivity, with implications for the evolution, development, plasticity, and function of the brain. Relative to previous models of cerebral connectivity that allowed relatively independent connectivity among any set of cortical areas, the grid structure of the present invention implies a marked reduction in the dimensionality of the space of cerebral fiber pathways. Developmentally, the grid structure of the present invention makes the problems of axonal navigation and path-finding simpler and more restricted than would independent regional connectivity. The grid structure of the present invention also provides a framework within which more complex connectivity may arise from simpler structure through incremental differential growth. Thus, the grid structure of the present invention, and the underlying coordinate system of the present invention that is representative of this grid structure, can be used to provide a natural substrate for gradual adaptation of connectivity, critical to plasticity and evolution.

It is contemplated that, functionally, the parallel pathways of the grid structure of the present invention helps preserve the spatial order and temporal coherence of signals over larger scales than would discrete fiber bundles. Thus, this grid structure may constitute a favorable substrate for neural coding utilizing topographic coherence and temporal synchrony. Spatiotemporal coherence can lead naturally to cortico-cortical mappings that preserve the local shapes of activation patterns. Thus, such cortico-cortical mappings are angle-preserving, or conformal, mappings between two-dimensional cortical areas. It is contemplated that the near-orthogonal three-dimensional structure of the fiber pathways would be a natural counterpart to two-dimensional conformal structure of cortical connectivity.

The implications of the grid structure of the present invention for brain mapping are several. First, it is contemplated that grid structure simplifies the description and quantification of the cerebral connectome by greatly reducing the dimensionality of its space of possible variation. This facilitates comparisons across groups and species, and between individuals. Second, a basic problem for diffusion MRI is the question of validation given the absence of effective gold-standards in humans. In this context, the grid structure of the present invention, and the underlying coordinate system representative of the grid structure, may contribute to validation of diffusion MRI of cerebral connectivity based on geometric self-consistency, such as the existence of geometrically well-defined sheets. Third, constraints represented by the grid structure of the present invention can improve biophysical models of cerebral diffusion and aid in the discovery and measurement of effective biomarkers for connectional diseases, such as multiple sclerosis. Fourth, as described above, the grid structure of the present invention is useful in the construction of natural coordinate systems for the brain The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing an image of a subject, the steps of the method comprising:
    a) acquiring image data of a brain of the subject that includes white matter tissue;
    b) reconstructing from the image data, an image of the subject that depicts the white matter tissue;
    c) producing coordinate system information by correlating the white matter tissue in the reconstructed image with a coordinate system in which the white matter tissue is arranged in a substantially orthogonal grid, and wherein tissue pathways in the white matter tissue are arranged along axes defining the substantially orthogonal grid; and
    d) providing the reconstructed image and the produced coordinate system information to a user.

2. The method as recited in claim 1 in which the produced coordinate system is centered with respect to an anatomical landmark of the subject.

3. The method as recited in claim 2 in which the anatomical landmark is at least one of a mid-line of the brain and an anterior commissure-posterior commissure line.

4. The method as recited in claim 1 in which white matter tissue arranged in the grid includes portions of white matter tissue that are interwoven with other portions of white matter tissue.

5. The method as recited in claim 1 in which white matter tissue arranged in the grid includes portions of white matter tissue arranged in sheets of parallel white matter fiber paths.

6. The method as recited in claim 5 in which white matter tissue arranged in the grid includes sheets of white matter tissue that are arranged substantially orthogonally to other sheets of white matter tissue.

7. The method as recited in claim 1 in which step c) includes selecting a white matter fiber path in the white matter tissue and identifying other white matter fiber paths adjacent to the selected white matter fiber path.

8. The method as recited in claim 7 in which step c) includes performing tractography on the images reconstructed in step b) to determine white matter fiber paths in the white matter tissue.

9. The method as recited in claim 7 in which step c) includes identifying a neighborhood of white matter fiber paths adjacent to the selected white matter fiber path.

10. The method as recited in claim 7 in which step c) includes assigning the selected white matter fiber path and the identified other white matter fiber paths a principal direction that is substantially aligned with cardinal axes of the subject.

11. The method as recited in claim 10 in which the principal direction is at least one of longitudinal, transverse, and dorsoventral.

12. A method for guiding processing of an image of a subject, the steps of the method comprising:
    a) acquiring image data of a subject that includes white matter tissue containing white matter fibers, the image data being sensitized to diffusion;
    b) reconstructing from the image data, an image of the subject that depicts the white matter tissue;
    c) defining, using the reconstructed image, a coordinate system particular to the subject and in which the white matter fibers of the white matter tissue are arranged along axes defining a substantially orthogonal grid; and
    d) processing an image of the subject using the defined coordinate system to produce a metric indicative of a characteristic of the subject.

13. The method as recited in claim 12 in which the image processed in step d) is the image reconstructed in step b), and step d) includes weighting the reconstructed image using the defined coordinate system to produce an image of the subject that is indicative of white matter fibers in the subject.

14. The method as recited in claim 13 in which the metric produced in step d) is a measurement of white matter fiber connectivity, and step d) includes determining a connectivity measure between two or more points in the reconstructed image using the defined coordinate system.

15. The method as recited in claim 13 in which the metric produced in step d) represents characteristics of white matter fibers in the subject at a different age of the subject, and step d) includes performing a regression on the image of the subject that is indicative of white matter fibers using the defined coordinate system.

16. The method as recited in claim 13 in which the metric produced in step d) is a measurement of an accuracy of the defined coordinate system.

17. The method as recited in claim 16 in which step d) includes calculating a closure gap in the defined coordinate system.

18. The method as recited in claim 12 in which the image is at least one of a T1-weighted magnetic resonance image, a T2-weighted magnetic resonance image, a diffusion weighted magnetic resonance image, a perfusion weighted medical image, a functional magnetic resonance image, and an angiographic medical image.

19. The method as recited in claim 12 in which the metric produced in step d) is an image depicting an average of images of multiple different subjects that are mapped into the defined coordinate system.

20. The method as recited in claim 12 in which the metric includes a measure of deviations of different white matter fibers from being arranged as one of substantially parallel to each other and substantially orthogonal to each other.

21. The method as recited in claim 20 in which the metric includes an angle of deviation that provides a marker for regional brain stretching.

22. The method as recited in claim 21 further comprising using the angle of deviation to determine an indication of at least one of brain growth, normal tissue structure, and deformity.

23. A non-transient computer readable storage medium having stored thereon instructions that when carried out by a processor direct the processor to perform a method, the steps of the method comprising:
a) acquiring image data of a brain of the subject that includes white matter tissue, the image data reflecting diffusion information about the white matter tissue;
b) defining from the image data, a coordinate system particular to the subject in which the white matter tissue is arranged along axes defining a substantially orthogonal grid;
c) correlate the defined coordinate system with the image data.

24. A method for determining white matter fiber paths in a brain of a subject using medical imaging data, the steps of the method comprising:
a) acquiring image data of the subject that includes information about the white matter tissue in the brain of the subject including diffusion information;
b) determining a first vector from the diffusion information potentially corresponding to a portion of a first white matter fiber path formed in the white matter tissue in the brain of the subject;
c) determining a second vector from the diffusion information potentially corresponding to a portion of a second white matter fiber path formed in the white matter tissue in the brain of the subject;
d) performing an interrelated tractography procedure using the diffusion data, the first vector, and the second vector, wherein the interrelated tractography procedure considers relative components of the first vector and the second vector to one another and vector marker constraints to evaluate a likelihood of correspondence to the first white matter fiber path and second white matter fiber path; and
e) building a representation of the first white matter fiber path and the second white matter fiber path formed in the white matter tissue in the brain of the subject.

25. The method as recited in claim 24 wherein step d) further includes determining extensions from the first vector and the second vector potentially corresponding to additional portions of the first white matter fiber path and the second white matter fiber, respectively, and considering relative components of the extensions from the first vector and the second vector to one another to evaluate a likelihood of correspondence to the first white matter fiber path and second white matter fiber path.

26. The method as recited in claim 24 further comprising producing coordinate system information by correlating the first vector and the second vector with a coordinate system in which the white matter tissue is arranged in a substantially orthogonal grid.

27. The method as recited in claim 26 in which the produced coordinate system is centered with respect to an anatomical landmark of the subject.

28. The method as recited in claim 27 in which the anatomical landmark is at least one of a mid-line of the brain and an anterior commissure-posterior commissure line.

29. The method as recited in claim 26 in which white matter tissue arranged in the grid includes at least one of portions of white matter tissue arranged in sheets of parallel white matter fiber paths and portions of white matter tissue interwoven with other portions of white matter tissue.

30. The method as recited in claim 29 in which white matter tissue arranged in the grid includes sheets of white matter tissue that are arranged substantially orthogonally to other sheets of white matter tissue.

31. The method as recited in claim 24 in which step d) includes assigning a principal direction of the first vector and the second vector corresponding to at least one of longitudinal, transverse, and dorsoventral.

32. A method for determining white matter fiber paths in a brain of a subject using medical imaging data, the steps of the method comprising:
a) acquiring image data of the subject that includes information about the white matter tissue in the brain of the subject including diffusion information;
b) determining a first vector from the diffusion information potentially corresponding to a portion of a first white matter fiber path formed in the white matter tissue in the brain of the subject;
c) determining a second vector from the diffusion information potentially corresponding to a portion of a second white matter fiber path formed in the white matter tissue in the brain of the subject;
d) determining a third vector from the diffusion information potentially corresponding to a portion of a third white matter fiber path formed in the white matter tissue in the brain of the subject;
e) assigning a principal direction of the first vector, the second vector, and the third vector corresponding to one of longitudinal, transverse, and dorsoventral orientations in the brain of the subject;
e) building a representation of the first white matter fiber path, the second white matter fiber path, and the third white matter fiber path considering vector marker constraints and relative components of the first vector, the second vector, and the third vector and the assigned principal direction to one another.

33. The method as recited in claim 32 in which step e) includes performing an interrelated tractography procedure using the diffusion data, the first vector, the second vector, and the third vector considering the vector marker constraints and relative components of the first vector, the second vector, and the third vector to one another to evaluate a likelihood of correspondence to the first white matter fiber path, second white matter fiber path, and the third white matter fiber path respectively.

34. A method for determining white matter tissue pathways in a brain of a subject, the steps of the method comprising:
a) acquiring image data of a brain of the subject that includes white matter tissue, the image data including diffusion information about the white matter tissue;
b) reconstructing from the image data, an image of the subject that depicts the white matter tissue;
c) generating coordinate system information by mapping at least one volume of interest in the reconstructed image onto a grid structure coordinate system in which white matter tissue is arranged substantially parallel to orthogonal axes defining the grid structure coordinate system;
d) determining constraints for white matter tissue pathways using the generated coordinate system information; and
e) performing an interrelated tractography procedure using the image data and constraints to determine white matter tissue pathways in the brain of the subject.

* * * * *